(12) United States Patent
Meade et al.

(10) Patent No.: US 9,139,844 B2
(45) Date of Patent: *Sep. 22, 2015

(54) COMBINED USE OF CRY1CA AND CRY1AB PROTEINS FOR INSECT RESISTANCE MANAGEMENT

(75) Inventors: Thomas Meade, Zionsville, IN (US); Aaron T. Woosley, Fishers, IN (US); Kenneth Narva, Zionsville, IN (US); Stephanie L. Burton, Indianapolis, IN (US); Nicholas P. Storer, Kensington, MD (US); Joel J. Sheets, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 419 days.

This patent is subject to a terminal disclaimer.

(21) Appl. No.: 13/516,615

(22) PCT Filed: Dec. 16, 2010

(86) PCT No.: PCT/US2010/060819
§ 371 (c)(1),
(2), (4) Date: Aug. 27, 2012

(87) PCT Pub. No.: WO2011/084622
PCT Pub. Date: Jul. 14, 2011

(65) Prior Publication Data
US 2012/0311745 A1  Dec. 6, 2012

Related U.S. Application Data

(60) Provisional application No. 61/284,292, filed on Dec. 16, 2009.

(51) Int. Cl.
*C12N 15/82* (2006.01)
*A01N 63/02* (2006.01)

(52) U.S. Cl.
CPC ............ *C12N 15/8286* (2013.01); *A01N 63/02* (2013.01)

(58) Field of Classification Search
None
See application file for complete search history.

(56) References Cited

U.S. PATENT DOCUMENTS

| 5,723,758 | A | | 3/1998 | Payne et al. |
|---|---|---|---|---|
| 5,866,784 | A | * | 2/1999 | Van Mellaert et al. ....... 800/302 |
| 5,990,390 | A | * | 11/1999 | Lundquist et al. ............ 800/302 |
| 6,114,608 | A | * | 9/2000 | Mettler et al. ............. 800/320.1 |
| 2003/0084606 | A1 | | 5/2003 | Parker |
| 2004/0133942 | A1 | | 7/2004 | Miles et al. |
| 2005/0155103 | A1 | | 7/2005 | Baum et al. |
| 2005/0216969 | A1 | | 9/2005 | Song et al. |
| 2008/0311096 | A1 | | 12/2008 | Lang et al. |
| 2010/0235951 | A1 | | 9/2010 | Van Rie et al. |

FOREIGN PATENT DOCUMENTS

| WO | WO 2008/073877 A2 | 7/2008 |
|---|---|---|
| WO | WO 2008/145406 A1 | 12/2008 |

OTHER PUBLICATIONS

Höfte et al (1986, Eur. J. Biochem. 161:273-280).*
Crickmore et al (2014 "Bacillus thuringiensis toxin nomenclature" http://www.btnomenclature.info/).*
Bates et al (2005, Nature Biotechnol. 23:57-62).*
González-Cabrera et al (2006, Appl. Environ. Microbiol. 72:2594-2600).*
Rang et al (2004, Current Microbiol. 49:22-27).*
Bravo, A. et al: "How to cope with insect resistance to Bt toxins?", Trends in Biotechno(Logy, Elsevier Publications, Cambridge, GB, vol. 26, No. 10. Oct. 1, 2008, pp. 573-579, XP025406825, ISSN: 0167-7799, DOI: 10.1016/J.tibtech. Jun. 5, 2008 [retrieved on Aug. 14, 2008].
Salm et al: "Insect resistance of transgenic plants that express modified *Bacillus thuringiensis* cry1A(b) and cry1C genes: a resistance managemetn strategy.", Plant Molecular Biology, vol. 28, 1994, pp. 51-59, XP001029215.
Gutierrez, et al. "Physiologically based demographics of Bt cotton-pest interactions i.", Pink Bollworm Resistance<Refuge and Risk Ecological Modelling, vol. 191, 2006, pp. 346-359, XP005239868.

* cited by examiner

*Primary Examiner* — Anne Kubelik
(74) *Attorney, Agent, or Firm* — Ronald S. Maciak; Faegre Baker Daniels LLP

(57) ABSTRACT

The subject invention includes methods and plants for controlling lepidopteran insects, said plants comprising Cry1Ca insecticidal protein and a Cry1Ab insecticidal protein in combination to delay or prevent development of resistance by the insects.

19 Claims, 2 Drawing Sheets

Figure 1 - Competition for binding to *Spodoptera frugiperda* BBMV's by Cry1Ab core toxin, Cry1Ca core toxin, and 125I-labeled Cry1Ca core toxin protein Figure 2 - Competition for binding to *Spodoptera frugiperda* BBMV's by Cry1Ca core toxin, Cry1Ab core toxin, and 125I-labeled Cry1Ab core toxin protein.

COMBINED USE OF CRY1CA AND CRY1AB PROTEINS FOR INSECT RESISTANCE MANAGEMENT

CROSS-REFERENCE TO RELATED APPLICATIONS

This is a national phase application, filed pursuant to 35 U.S.C. §371, of PCT application No. PCT/US10/60819 filed on Dec. 16, 2010, which claims the benefit of U.S. provisional application No. 61/284,292, filed on Dec. 16, 2009. The prior applications are incorporated herein by reference in their entirety.

BACKGROUND OF THE INVENTION

Humans grow corn for food and energy applications. Humans also grow many other crops, including soybeans and cotton. Insects eat and damage plants and thereby undermine these human efforts. Billions of dollars are spent each year to control insect pests and additional billions are lost to the damage they inflict. Synthetic organic chemical insecticides have been the primary tools used to control insect pests but biological insecticides, such as the insecticidal proteins derived from *Bacillus thuringiensis* (Bt), have played an important role in some areas. The ability to produce insect-resistant plants through transformation with Bt insecticidal protein genes has revolutionized modern agriculture and heightened the importance and value of insecticidal proteins and their genes.

Several Bt proteins have been used to create the insect-resistant transgenic plants that have been successfully registered and commercialized to date. These include Cry1Ab, Cry1Ac, Cry1Fa and Cry3Bb in corn, Cry1Ac and Cry2Ab in cotton, and Cry3A in potato.

The commercial products expressing these proteins express a single protein except in cases where the combined insecticidal spectrum of 2 proteins is desired (e.g, Cry1Ab and Cry3Bb in corn combined to provide resistance to lepidopteran pests and rootworm, respectively) or where the independent action of the proteins makes them useful as a tool for delaying the development of resistance in susceptible insect populations (e.g., Cry1Ac and Cry2Ab in cotton combined to provide resistance management for tobacco budworm).

That is, some of the qualities of insect-resistant transgenic plants that have led to rapid and widespread adoption of this technology also give rise to the concern that pest populations will develop resistance to the insecticidal proteins produced by these plants.

Several strategies have been suggested for preserving the utility of Bt-based insect resistance traits which include deploying proteins at a high dose in combination with a refuge, and alternation with, or co-deployment of, different toxins (McGaughey et al. (1998), "B.t. Resistance Management," *Nature Biotechnol.* 16:144-146).

The proteins selected for use in an insect resistance management (IRM) stack need to exert their insecticidal effect independently so that resistance developed to one protein does not confer resistance to the second protein (i.e., there is not cross resistance to the proteins). If, for example, a pest population selected for resistance to "Protein A" is sensitive to "Protein B", one would conclude that there is not cross resistance and that a combination of Protein A and Protein B would be effective in delaying resistance to Protein A alone.

In the absence of resistant insect populations, assessments can be made based on other characteristics presumed to be related to mechanism of action and cross-resistance potential. The utility of receptor-mediated binding in identifying insecticidal proteins likely to not exhibit cross resistance has been suggested (van Mellaert et al. 1999). The key predictor of lack of cross resistance inherent in this approach is that the insecticidal proteins do not compete for receptors in a sensitive insect species.

In the event that two B.t. Cry toxins compete for the same receptor, then if that receptor mutates in that insect so that one of the toxins no longer binds to that receptor and thus is no longer insecticidal against the insect, it might also be the case that the insect will also be resistant to the second toxin (which competitively bound to the same receptor). However, if two toxins bind to two different receptors, this could be an indication that the insect would not be simultaneously resistant to those two toxins.

Cry1Ab is an insecticidal protein currently used in transgenic corn to protect plants from a variety of insect pests. A key pest of corn that Cry1Ab provides protection from is the European corn borer.

Additional Cry toxins are listed at the website of the official B.t. nomenclature committee (Crickmore et al.; lifesci.sussex.ac.uk/home/Neil_Crickmore/Bt/). See Appendix A, attached. There are currently nearly 60 main groups of "Cry" toxins (Cry1-Cry59), with additional Cyt toxins and VIP toxins and the like. Many of each numeric group have capital-letter subgroups, and the capital letter subgroups have lower-cased letter sub-subgroups. (Cry1 has A-L, and Cry1A has a-i, for example).

BRIEF SUMMARY OF THE INVENTION

The subject invention relates in part to the surprising discovery that Cry1Ca is very active against sugarcane borer including a sugarcane borer population that is resistant to Cry1Ab. As one skilled in the art will recognize with the benefit of this disclosure, plants producing Cry1Ca and Cry1Ab (including insecticidal portions thereof), will be useful in delaying or preventing the development of resistance to either of these insecticidal proteins alone. A cry1Fa gene, for example, could also be stacked with these two base pair genes/proteins.

The subject invention also relates to the discovery that Cry1Ca and Cry1Ab do not compete with each other for binding gut receptors from fall armyworm (*Spodoptera frugiperda*; FAW).

BRIEF DESCRIPTION OF THE FIGURES

FIG. 1-Competition for binding to *Spodoptera frugiperda* BBMV's by Cry1Ab core toxin, Cry1Ca core toxin, and 125I-labeled Cry1Ca core toxin protein FIG. 2-Competition for binding to *Spodoptera frugiperda* BBMV's by Cry1Ca core toxin, Cry1Ab core toxin, and 125I-labeled Cry1Ab core toxin protein.

BRIEF DESCRIPTION OF THE SEQUENCE

SEQ ID NO:1—Cry1Ca core/Cry1Ab protoxin chimeric protein 1164 aa (DIG-152)
SEQ ID NO:2—a Cry1Ca core toxin
SEQ ID NO:3—a Cry1Ab core toxin

DETAILED DESCRIPTION OF THE INVENTION

The subject invention relates in part to the surprising discovery that Cry1Ca is very active against a sugarcane borer (SCB; *Diatraea saccharalis*) population that is resistant to Cry1Ab. Accordingly, the subject invention relates in part to the surprising discovery that Cry1Ca can be used in combination with, or "stacked" with, Cry1Ab to combat the development of resistance to either of these insecticidal proteins alone. Stated another way, the subject invention relates in part to the surprising discovery that that a sugarcane borer population selected for resistance to Cry1Ab is not resistant to Cry1Ca; sugarcane borer that are resistant to Cry1Ab toxin are susceptible (i.e., are not cross-resistant) to Cry1Ca. Thus, the subject invention includes the use of Cry1Ca toxin to control populations of sugarcane borer that are resistant to Cry1Ab.

As one skilled in the art will recognize with the benefit of this disclosure, plants expressing Cry1Ca and Cry1Ab (including insecticidal portions thereof), will be useful in delaying or preventing the development of resistance to either of these insecticidal proteins alone.

The subject invention includes the use of Cry1Ca to protect sugarcane and other economically important plant species from damage and yield loss caused by sugarcane borer or to sugarcane borer populations that have developed resistance to Cry1Ab. The sugarcane borer can also be a pest of corn. This is particularly true in some Central and South American countries such as Brazil and Argentina. Thus, corn, for example, can also be protected according to the subject invention.

The subject invention thus teaches an insect resistance management (IRM) stack to prevent or mitigate the development of resistance by sugarcane borer to Cry1Ab and/or Cry1Ca.

In addition, receptor binding studies using radiolabeled Cry1Ca and *Spodoptera frugipera*; fall armyworm (FAW) insect tissues show that Cry1Ab does not compete for the high affinity binding site to which Cry1Ca binds. These results indicate that the combination of Cry1Ab and Cry1Ca can be used as an effective means to mitigate the development of resistance in insect populations (such as FAW and SCB) to Cry1Ab and/or Cry1Ca for plants (such as maize and sugarcane) producing both proteins. While toxin overlay studies demonstrated that Cry1Ca protein bound to two proteins in BBMV's from *S. frugiperda*, one of 40 kDa and one of 44 kDa, whereas Cry1Ab protein bound to a single protein of 150 kDa (Aranda et al., 1996), that did not relate to non-competitive binding studies.

Thus, the subject invention also includes the combination of Cry1Ca and Cry1Ab as an IRM stack to mitigate against the development of resistance by fall armyworm and/or sugarcane borer to either protein, or to sugarcane borer populations that have developed resistance to Cry1Ab.

The present invention provides compositions for controlling lepidopteran pests comprising cells that express a Cry1Ca core toxin-containing protein and a Cry1Ab core toxin-containing protein;

a host transformed to express both a Cry1Ab core toxin-containing protein and a Cry1C core toxin containing protein, wherein said host is a microorganism or a plant cell (the subject polynucleotide(s) are preferably in a genetic construct under control of (operably linked to/comprising) a non-*Bacillus-thuringiensis* promoter; the subject polynucleotides can comprise codon usage for enhanced expression in a plant);

a method of controlling lepidopteran pests comprising contacting said pests or the environment of said pests with an effective amount of a composition that produces a Cry1Ab core toxin-containing protein and a cell expressing a Cry1C core toxin-containing protein;

a plant (such as a maize plant, or soybeans or cotton or sugarcane, for example) comprising DNA encoding a Cry1Ca core toxin-containing protein and DNA encoding a Cry1Ab core toxin-containing protein, and seed of such a plant;

a plant (such as a maize plant, or soybeans or cotton or sugarcane, for example) wherein DNA encoding a Cry1Ca core toxin-containing protein and DNA encoding a Cry1Ab core toxin-containing protein have been introgressed into said maize plant, and seed of such a plant.

We demonstrated, for example, that Cry1Ca (protein from recombinant *Pseudomonas fluorescens* strain MR1206/DC639; plasmid pMYC2547) is very effective in controlling sugarcane borer (SCB; *Diatraea saccharalis*) populations, in artificial diet bioassays, that have been selected for resistance to Cry1Ab. This indicates that Cry1Ca is useful in controlling SCB populations that have developed resistance to Cry1Ab or in mitigating the development of Cry1Ab resistance in SCB populations.

Based in part on the data described herein, co-expressing Cry1Ca and Cry1Ab can produce a high dose IRM stack for controlling SCB. Other proteins can be added to this combination to add spectrum. For example in corn, the addition of Cry1Fa would create an IRM stack for European corn borer (ECB), *Ostrinia nubilalis* (Hübner), while adding yet another MOA for control of SCB.

For a review of Cry1C as a potential bioinsecticide in plants, see (Avisar et al. 2009). Avisar D, Eilenberg H, Keller M, Reznik N, Segal M, Sneh B, Zilberstein A (2009) The *Bacillus thuringiensis* delta-endotoxin Cry1C as a potential bioinsecticide in plants. Plant Science 176:315-324.

Insect Receptors.

As described in the Examples, competitive receptor binding studies using radiolabeled Cry1Ca core toxin protein show that the Cry1Ab core toxin protein does not compete for the high affinity binding site present in FAW insect tissues to which Cry1Ca binds. These results indicate that the combination of Cry1Ab and Cry1Ca proteins would be an effective means to mitigate the development of resistance in FAW populations to Cry1Ab (and likewise, the development of resistance to Cry1Ca), and would likely increase the level of resistance to this pest in corn plants expressing both proteins.

These data also suggest that Cry1Ca would be effective in controlling SCB populations that have developed resistance to Cry1Ab. One deployment option would be to use these Cry proteins in geographies where Cry1Ab has become ineffective in controlling SCB due to the development of resistance. Another deployment option would be to use Cry1Ca in combination with Cry1Ab to mitigate the development of resistance in SCB to Cry1Ab.

Combinations of the toxins described in the invention can be used to control lepidopteran pests. Adult lepidopterans, i.e., butterflies and moths, primarily feed on flower nectar. The larvae, i.e., caterpillars, nearly all feed on plants, and many are serious pests. Caterpillars feed on or inside foliage or on the roots or stem of a plant, depriving the plant of nutrients and often destroying the plant's physical support structure. Additionally, caterpillars feed on fruit, fabrics, and stored grains and flours, ruining these products for sale or severely diminishing their value. As used herein, reference to lepidopteran pests refers to various life stages of the pest, including larval stages.

The chimeric toxins of the subject invention comprise a full core N-terminal toxin portion of a B.t. toxin and, at some point past the end of the toxin portion, the protein has a transition to a heterologous protoxin sequence. The N-terminal toxin portion of a B.t. toxin is referred to herein as the "core" toxin. The transition to the heterologous protoxin segment can occur at approximately the toxin/protoxin junction or, in the alternative, a portion of the native protoxin (extending past the toxin portion) can be retained with the transition to the heterologous protoxin occurring downstream.

As an example, one chimeric toxin of the subject invention has the full core toxin portion of Cry1Ab (amino acids 1 to 601) and a heterologous protoxin (amino acids 602 to the C-terminus). In one preferred embodiment, the portion of a chimeric toxin comprising the protoxin is derived from a Cry1Ab protein toxin. As a second Example, a second chimeric toxin of the subject invention, as disclosed in SEQ ID NO:1 (DIG-152) has the full core toxin portion of Cry1Ca (amino acids 1 to 619) and a heterologous protoxin (amino acids 620 to the C-terminus). In a preferred embodiment, the portion of a chimeric toxin comprising the protoxin is derived from a Cry1Ab protein toxin.

A person skilled in this art will appreciate that B.t. toxins, even within a certain class such as Cry1Ca, will vary to some extent in length and the precise location of the transition from toxin portion to protoxin portion. Typically, the cry1Ca toxins are about 1150 to about 1200 amino acids in length. The transition from toxin portion to protoxin portion will typically occur at between about 50% to about 60% of the full length toxin. The chimeric toxin of the subject invention will include the full expanse of this core N-terminal toxin portion. Thus, the chimeric toxin will comprise at least about 50% of the full length cry1Ca or Cry1Ab B.t. toxin. This will typically be at least about 590 amino acids. With regard to the protoxin portion, the full expanse of the Cry1A(b) protoxin portion extends from the end of the toxin portion to the C-terminus of the molecule. It is the last about 100 to 150 amino acids of this portion which are most critical to include in the chimeric toxin of the subject invention.

Genes and Toxins.

The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

As used herein, the boundaries represent approximately 95% (Cry1Ab's and 1Ca's), 78% (Cry1A's and Cry1C's), and 45% (Cry1's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813. These cut offs can also be applied to the core toxins only (for Cry1Ab and Cry1C toxins). The GENBANK numbers listed in the attached Appendix A can also be used to obtain the sequences for any of the genes and proteins disclosed or mentioned herein.

It should be apparent to a person skilled in this art that genes encoding active toxins can be identified and obtained through several means. The specific genes or gene portions exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the gene-encoding toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) DNA Probes, Stockton Press, New York, N.Y., pp. 169-170. Some examples of salt concentrations and temperature combinations are as follows (in order of increasing stringency): 2×SSPE or SSC at room temperature; 1×SSPE or SSC at 42° C.; 0.1×SSPE or SSC at 42° C.; 0.1×SSPE or SSC at 65° C. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using DNA synthesizer and standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gly |
| Acidic | Asp, Glu |
| Basic | Lys, Arg, His |

In some instances, non-conservative substitutions can also be made. The critical factor is that these substitutions must not significantly detract from the biological activity of the toxin.

Recombinant hosts. The genes encoding the toxins of the subject invention can be introduced into a wide variety of microbial or plant hosts. Expression of the toxin gene results, directly or indirectly, in the intracellular production and maintenance of the pesticide. Conjugal transfer and recombinant transfer can be used to create a B.t. strain that expresses both toxins of the subject invention. Other host organisms may also be transformed with one or both of the toxin genes then used to accomplish the synergistic effect. With suitable microbial hosts, e.g., *Pseudomonas*, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobactenum, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobactenium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. *Bacillus thuringiensis* or recombinant cells expressing the B.t. toxins can be treated to prolong the toxin activity and stabilize the cell. The pesticide microcapsule that is formed comprises the B.t. toxin or toxins within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene or genes, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene or genes into the host, availability of expression systems, efficiency of expression, stability of the pesticide in the host, and the presence of auxiliary genetic capabilities.

Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene or genes may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells producing the toxins of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations.

Formulated bait granules containing an attractant and spores, crystals, and toxins of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., foliage or soil, by spraying, dusting, sprinkling, or the like.

Plant Transformation.

A preferred recombinant host for production of the insecticidal proteins of the subject invention is a transformed plant. Genes encoding Bt toxin proteins, as disclosed herein, can be inserted into plant cells using a variety of techniques which are well known in the art. For example, a large number of cloning vectors comprising a replication system in *Escherichia coli* and a marker that permits selection of the transformed cells are available for preparation for the insertion of foreign genes into higher plants. The vectors comprise, for example, pBR322, pUC series, M13 mp series, pACYC184, inter alia. Accordingly, the DNA fragment having the sequence encoding the Bt toxin protein can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516, Lee and Gelvin (2008), Hoekema (1985), Fraley et al., (1986), and An et al., (1985), and is well established in the art.

Once the inserted DNA has been integrated in the plant genome, it is relatively stable. The transformation vector normally contains a selectable marker that confers on the transformed plant cells resistance to a biocide or an antibiotic, such as Bialaphos, Kanamycin, G418, Bleomycin, or Hygromycin, inter alia. The individually employed marker should accordingly permit the selection of transformed cells rather than cells that do not contain the inserted DNA.

A large number of techniques is available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the Right and Left T-DNA border regions. They can be transformed directly into *Agrobacteria* (Holsters et al., 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. While some truncated toxins are exemplified herein, it is well-known in the Bt art that 130 kDa-type (full-length) toxins have an N-terminal half that is the core toxin, and a C-terminal half that is the protoxin "tail." Thus, appropriate "tails" can be used with truncated/core toxins of the subject invention. See e.g. U.S. Pat. No. 6,218,188 and U.S. Pat. No. 6,673,990. In addition, methods for creating synthetic Bt genes for use in plants are known in the art (Stewart and Burgin, 2007). One non-limiting example of a preferred transformed plant is a fertile maize plant comprising a plant expressible gene encoding a Cry1Fa protein, and further comprising a second plant expressible gene encoding a Cry1Ca protein.

Transfer (or introgression) of the Cry1Ab and Cry1C trait(s) into inbred maize lines can be achieved by recurrent selection breeding, for example by backcrossing. In this case, a desired recurrent parent is first crossed to a donor inbred (the non-recurrent parent) that carries the appropriate gene(s) for the Cry1Ab and Cry1C traits. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376).

Insect Resistance Management (IRM) Strategies.

Roush et al., for example, outlines two-toxin strategies, also called "pyramiding" or "stacking," for management of insecticidal transgenic crops. (The Royal Society. *Phil. Trans. R. Soc. Lond. B*. (1998) 353, 1777-1786). On their website, the United States Environmental Protection Agency (ep-a.gov/oppbppd1/biopesticides/pips/bt_corn_refuge_2006.htm) publishes the following requirements for providing non-transgenic (i.e., non-B. t.) refuges (a block of non-Bt crops/corn) for use with transgenic crops producing a single Bt protein active against target pests.

The specific structured requirements for corn borer-protected Bt (Cry1Ab or Cry1F) corn products are as follows:
Structured refuges:
  20% non-Lepidopteran Bt corn refuge in Corn Belt
  50% non-Lepidopteran Bt refuge in Cotton Belt
  Blocks
    1. Internal (i.e., within the Bt field)
    2. External (i.e., separate fields within ½ mile (¼ mile if possible) of the Bt field to maximize random mating)
  In-field Strips
    Strips must be at least 4 rows wide (preferably 6 rows) to reduce the effects of larval movement The National Corn Growers Association, on their website (ncga.com/insect-resistance-management-fact-sheet-bt-corn), also provides similar guidance regarding the requirements. For example:
Requirements of the Corn Borer IRM:
  Plant at least 20% of your corn acres to refuge hybrids
  In cotton producing regions, refuge must be 50%
  Must be planted within ½ mile of the refuge hybrids
  Refuge can be planted as strips within the Bt field; the refuge strips must be at least 4 rows wide
  Refuge may be treated with conventional pesticides only if economic thresholds are reached for target insect
  Bt-based sprayable insecticides cannot be used on the refuge corn
  Appropriate refuge must be planted on every farm with Bt corn As stated by Roush et al. (on pages 1780 and 1784 right column, for example), stacking or pyramiding of two different proteins each effective against the target pests and with little or no cross-resistance can allow for use of a smaller refuge. Roush suggests that for a successful stack, a refuge size of less than 10% refuge, can provide comparable resistance management to about 50% refuge for a single (non-pyramided) trait. For currently available pyramided Bt corn products, the U.S. Environmental Protection Agency requires significantly less (generally 5%) structured refuge of non-Bt corn be planted than for single trait products (generally 20%).

Any of the above percentages (such as those for 1F/1Ab), or similar refuge ratios, can be used for the subject double or triple stacks or pyramids. The subject invention includes commercial acreage—of over 10 acres for example—planted with (or without) such refuge and with plants according to the subject invention.

There are various ways of providing the refuge, including various geometric planting patterns in the fields (as mentioned above), to in-bag seed mixtures, as discussed further by Roush and, for example, U.S. Pat. No. 6,551,962.

All patents, patent applications, provisional applications, and publications referred to or cited herein are incorporated by reference in their entirety to the extent they are not inconsistent with the explicit teachings of this specification. Unless specifically indicated or implied, the terms "a", "an", and "the" signify "at least one" as used herein.

The following examples illustrate the invention. The examples should not be construed as limiting.

Example 1

Design of Chimeric Toxins Comprising Cry1 Core Toxins and Heterologous Protoxins, and Insecticidal Activity of Dig-152 Protein Produced in *Pseudomonas fluorescens*

Chimeric Toxins.

Chimeric proteins utilizing the core toxin domain of one Cry toxin fused to the protoxin segment of another Cry toxin have previously been reported, for example, in U.S. Pat. No. 5,593,881 and U.S. Pat. No. 5,932,209.

Cry1Ca chimeric protein variants of this invention include chimeric toxins comprising an N-terminal core toxin segment derived from a Cry1Ca3 insecticidal toxin fused to a heterologous delta endotoxin protoxin segment at some point past the end of the core toxin segment. The transition from the core toxin to the heterologous protoxin segment can occur at approximately the native core toxin/protoxin junction, or a portion of the native protoxin (extending past the core toxin segment) can be retained, with the transition to the heterologous protoxin occurring downstream. In variant fashion, the core toxin and protoxin segments may comprise exactly the amino acid sequence of the native toxins from which they are derived, or may include amino acid additions, deletions, or substitutions that do not diminish, and may enhance, the biological function of the segments when fused to one another.

For example, a chimeric toxin of the subject invention comprises a core toxin segment derived from Cry1Ca3 and a heterologous protoxin. In a preferred embodiment of the invention, the core toxin segment derived from Cry1Ca3 (619 amino acids) is fused to a heterologous segment comprising a protoxin segment derived from a Cry1Ab delta-endotoxin (545 amino acids). The 1164 amino acid sequence of the chimeric protein, herein referred to as DIG-152, is disclosed as SEQ ID NO:1. It is to be understood that other chimeric fusions comprising Cry1Ca3 core toxin variants and protoxins derived from Cry1Ab are within the scope of this invention.

Lepidopteran insecticidal activity of the DIG-152 protein was demonstrated on neonate larvae of sugarcane borer (SCB; *Diatraea saccharalis*) and Cry1Ab-resistant SCB (rSCB) in dose-response experiments utilizing diet incorporation procedures. DIG-152 inclusion bodies were solubilized by rocking gently at 4° for 4 hrs in 7.5 mL of 100 mM CAPS pH11, 1 mM EDTA, to which had been added 200 µL of bacterial protease inhibitor (Sigma P4865; prepared per supplier's instructions). Following centrifugation to pellet the insoluble material, the stock protein concentration was adjusted to 4.0 mg/mL in 100 mM CAPS, pH11. For insect bioassay, DIG-152 protein concentrations in the range of 0.030 µg to 102 µg/gm diet were prepared by mixing appropriate volumes with a meridic diet (Bio-Serv, Frenchtown, N.J.) just prior to dispensing approximately 0.7 mL of the diet into individual cells of 128-cell trays (Bio-Ba-128, C-D International).

Trypsin-activated Cry1Ab protein (used as a positive control for insecticidal activity) was tested in the range of 0.03125 µg to 32 µg/gm diet (prepared by mixing lyophilized powder with appropriate amounts of distilled water before diet preparation).

Diets prepared with distilled water (Blank Control, for Cry1Ab tests) or Buffer Only (100 mM CAPS pH11, for DIG-152 tests) were used as control treatments. One neonate larva of *D. saccharalis* (<24 hr after eclosion) was released on the diet surface in each cell. After larval inoculation, cells were covered with vented lids (C-D International) and the bioassay trays were placed in an environmental chamber maintained at 28°, 50% RH, and a 16 hr:8 hr (light:dark) photoperiod. Larval mortality, larval weight, and number of surviving larvae that did not demonstrate weight gains (<0.1 mg per larva) were recorded on the seventh day after inoculation. Each combination of insect strain/Cry protein concentration was replicated four times, with 16 to 32 larvae in each replicate.

Larval mortality criteria were measured as "practical" mortality, which considered both the Dead (morbid) larvae and the surviving (Stunted, non-feeding) larvae that did not show a significant gain in body weight (i.e. <0.1 mg per larva). The practical mortality of larvae in a treatment was calculated using the equation:

$$\text{Practical Mortality}(\%) = [TDS/TNIT] \times 100$$

where TDS is the Total number of Dead larvae plus the number of Stunted larvae, and TNIT is the Total Number of Insects in the Treatment The "practical" mortality (hereafter simplified as Mortality) of each *D. saccharalis* strain was corrected for larval mortality observed on water Blank Control diet for analyzing results following Cry1Ab treatment, or the Buffer Only-treated diet for the DIG-152 treatment.

The results of the dose response experiments were further analyzed to establish a $GI_{50}$ value, [i.e. the concentration of B.t. protein in the diet at which the larval growth inhibition (% GI) value was 50]. The % GI value of larvae on diet containing Cry1Ab-protein was calculated using the formula:

$$\% GI = [TWC - TWT]/TWC \times 100$$

where TWC is the Total body Weight of larvae feeding on water Control diet, and

TWT is the Total body Weight of larvae feeding on Cry1Ab Treated diet whereas, for analyzing larval % GI as a result of DIG-152 protein ingestion, it was calculated using the formula:

$$\% GI = [TWB - TWT]/TWB \times 100$$

where TWB is the Total body Weight of larvae feeding on Buffer-Only control treated diet, and TWT is the Total body Weight of larvae feeding on DIG-152 Treated diet A larval growth inhibition of 100% was assigned to a replication if there were no larvae that had significant weight gain (<0.1 mg per larva). The growth inhibition data were analyzed using a two-way ANOVA with insect strain and Cry protein concentration as the two main factors. LSMEANS tests were used to determine treatment differences at the α=0.05 level.

The results of the diet-incorporation bioassays on *Diatraea saccharalis* larvae are given in Table 2.

TABLE 2

Dose response larval mortality and growth inhibition (% mean ± sem) of Cry1Ab -susceptible (SCB) and Cry1Ab-resistant (rSCB) *Diatraea saccharalis* feeding on diet containing Cry1Ab or DIG-152 protein[a]

| | Cry1Ab protein | | | | DIG-152 | | | |
|---|---|---|---|---|---|---|---|---|
| Insect | protein conc'n[b] | # larvae | Mortality[c] | % GI[d] | protein conc'n[b] | # larvae | Mortality[c] | % GI[e] |
| SCB | Blank | 126 | 3.2 ± 1.3 a | — | Blank | 124 | 10.4 ± 3.2 b | 5.9 ± 4.8 a |
| rSCB | Blank | 128 | 4.7 ± 2.0 a | — | Blank | 125 | 4.1 ± 2.5 a | 3.1 ± 5.5 a |
| SCB | Buffer | NT[f] | | | Buffer | 121 | 10.9 ± 3.9 b | — |
| rSCB | Buffer | NT | | | Buffer | 127 | 1.6 ± 0.9 a | — |
| SCB | 0.03125 | 124 | 38.6 ± 4.8 c | 90.7 ± 1.6 ef | 0.03 | 126 | 53.1 ± 2.3 c | 69.5 ± 6.5 c |
| rSCB | 0.03125 | 123 | 8.3 ± 3.2 ab | −15.9 ± 4.6 a | 0.03 | 127 | 3.2 ± 0.0 a | 8.0 ± 5.1 a |
| SCB | 0.125 | 128 | 34.3 ± 7.9 c | 87.4 ± 2.5 e | 0.1 | 127 | 88.2 ± 3.5 d | 100 ± 0.0 d |
| rSCB | 0.125 | 126 | 8.6 ± 2.3 ab | 10.0 ± 5.3 b | 0.1 | 127 | 11.8 ± 0.8 b | 49.0 ± 3.5 b |

TABLE 2-continued

Dose response larval mortality and growth inhibition (% mean ± sem) of Cry1Ab -susceptible (SCB) and Cry1Ab-resistant (rSCB) *Diatraea saccharalis* feeding on diet containing Cry1Ab or DIG-152 protein[a]

| | Cry1Ab protein | | | | DIG-152 | | | |
|---|---|---|---|---|---|---|---|---|
| Insect | protein conc'n[b] | # larvae | Mortality[c] | % GI[d] | protein conc'n[b] | # larvae | Mortality[c] | % GI[e] |
| SCB | 0.5 | 119 | 75.6 ± 2.9 e | 94.3 ± 1.0 fg | 0.4 | 130 | 96.2 ± 1.9 e | 100 ± 0.0 d |
| rSCB | 0.5 | 128 | 5.5 ± 1.5 a | 26.7 ± 3.1 c | 0.4 | 125 | 91.2 ± 2.0 d | 100 ± 0.0 d |
| SCB | 2 | 125 | 93.6 ± 2.2 f | 100 ± 0.0 g | 1.6 | 122 | 100 ± 0.0 f | 100 ± 0.0 d |
| rSCB | 2 | 128 | 14.8 ± 2.7 b | 67.5 ± 1.5 d | 1.6 | 127 | 100 ± 0.0 f | 100 ± 0.0 d |
| SCB | 8 | 122 | 95.9 ± 1.6 fg | 100 ± 0.0 g | 6.4 | 125 | 100 ± 0.0 f | 100 ± 0.0 d |
| rSCB | 8 | 120 | 40.6 ± 5.1 c | 85.2 ± 1.9 e | 6.4 | 128 | 100 ± 0.0 f | 100 ± 0.0 d |
| SCB | 32 | 126 | 99.2 ± 0.8 g | 100 ± 0.0 g | 25.6 | 78 | 100 ± 0.0 f | 100 ± 0.0 d |
| rSCB | 32 | 128 | 60.9 ± 5.8 d | 90.3 ± 2.2 ef | 25.6 | 119 | 100 ± 0.0 f | 100 ± 0.0 d |
| SCB | | | | | 102 | 60 | 100 ± 0.0 f | 100 ± 0.0 d |
| rSCB | | | | | 102 | 126 | 100 ± 0.0 f | 100 ± 0.0 d |

[a]Mean values within a column across all treatments followed by a same letter are not significantly different ($P < 0.05$; LSMEANS test).
sem = standard error of the mean
[b]μg protein/gm diet
[c]The measure of larval mortality was as defined in the text.
[d]These percent values were calculated using the formula described in the text.
[e]These percent values were calculated using the formula described in the text.
[f]NT = Not Tested Data Analysis.

Corrected dose/mortality data then were subjected to probit analysis for determining treatment protein concentrations that caused a 50% mortality ($LC_{50}$) value and the corresponding 95% confidence intervals (CI). The treatments used in the probit analysis included the highest concentration that produced zero mortality, the lowest concentration that resulted in 100% mortality, and all results between those extremes. Resistance ratios were calculated by dividing the $LC_{50}$ value of the rSCB strain by that of the SCB insects. A lethal dose ratio test was used to determine if the resistance ratios were significant at $\alpha=0.05$ level. A two-way ANOVA also was used to analyze the mortality data, followed by the LSMEANS test at the $\alpha=0.05$ level to determine treatment differences. The results of the analyses are presented in Table 3.

TABLE 3

Summary of bioassay tests on larvae of SCB and rSCB using insect diet into which DIG-152 protein or Cry1Ab protein was incorporated.

| | Insect | # larvae tested | $LC_{50}$ (95% CI) (μg/gm)[a] | RR[b] |
|---|---|---|---|---|
| DIG-152 | SCB | 505 | 0.03 (0.02-0.03) | 6.0 NS |
| | rSCB | 506 | 0.18 (0.15-0.24) | |
| Cry1Ab | SCB | 744 | 0.13 (0.08-0.20 | 142 S |
| | rSCB | 440 | 18.46 (13.93-26.29 | |

[a]The measure of larval mortality was defined as described in the text.
[b]Resistance ratios with a letter 'S' are Significant, while those with letters 'NS' are Not Significant at the 5% level based on lethal dose tests.

It is a feature of the DIG-152 protein of the subject invention that the growth of neonate sugarcane borer (*Diatraea saccharalis*) larvae is inhibited, or the larvae are killed, following ingestion of DIG-152 protein at levels similar to those of activated Cry1Ab protein which give the same biological response. It is a further feature of the DIG-152 protein that *Diatraea saccharalis* larvae that are resistant to the toxic effects of Cry1Ab protein are nonetheless susceptible to the toxic action of the DIG-152 protein.

Example 2

Construction of Expression Plasmids Encoding Chimeric Proteins and Expression in *Pseudomonas*

Standard cloning methods [as described in, for example, Sambrook et al., (1989) and Ausubel et al., (1995), and updates thereof] were used in the construction of *Pseudomonas fluorescens* (Pf) expression construct pMYC2547 engineered to produce a full-length DIG-152 chimeric protein. Protein production was performed in *Pseudomonas fluorescens* strain MB214 (a derivative of strain MB101; *P. fluorescens* biovar I), having an insertion of a modified lac operon as disclosed in U.S. Pat. No. 5,169,760. The basic cloning strategy entailed subcloning a DNA fragment encoding DIG-152 into plasmid vectors, whereby it is placed under the expression control of the Ptac promoter and the rrnBT1T2 terminator from plasmid pKK223-3 (PL Pharmacia, Milwaukee, Wis.). One such plasmid was named pMYC2547, and the MB214 isolate harboring this plasmid is named Dpf108.

Growth and Expression Analysis in Shake Flasks

Production of DIG-152 protein for characterization and insect bioassay was accomplished by shake-flask-grown *P. fluorescens* strain Dpf108. DIG-152 protein production driven by the Ptac promoter was conducted as described previously in U.S. Pat. No. 5,527,883. Details of the microbiological manipulations are available in Squires et al., (2004), US Patent Application 20060008877, US Patent Application 20080193974, and US Patent Application 20080058262, incorporated herein by reference. Expression was induced by addition of isopropyl-β-D-1-thiogalactopyranoside (IPTG) after an initial incubation of 24 hours at 30° with shaking Cultures were sampled at the time of induction and at various times post-induction. Cell density was measured by optical density at 600 nm ($OD_{600}$).

Cell Fractionation and SDS-PAGE Analysis of Shake Flask Samples

At each sampling time, the cell density of samples was adjusted to $OD_{600}=20$ and 1 mL aliquots were centrifuged at 14000×g for five minutes. The cell pellets were frozen at −80°. Soluble and insoluble fractions from frozen shake flask cell pellet samples were generated using EasyLyse™ Bacterial Protein Extraction Solution (EPICENTRE® Biotechnologies, Madison, Wis.). Each cell pellet was resuspended in 1 mL EasyLyse™ solution and further diluted 1:4 in lysis buffer and incubated with shaking at room temperature for 30 minutes. The lysate was centrifuged at 14,000 rpm for 20 minutes at 4° and the supernatant was recovered as the soluble fraction. The pellet (insoluble fraction) was then resuspended in an equal volume of phosphate buffered saline (PBS; 11.9 mM $Na_2HPO_4$, 137 mM NaCl, 2.7 mM KCl, pH7.4).

Samples were mixed 1:1 with 2× Laemmli sample buffer containing β-mercaptoethanol (Sambrook et al., supra.) and boiled for 5 minutes prior to loading onto Criterion XT Bis-Tris 12% gels (Bio-Rad Inc., Hercules, Calif.). Electrophoresis was performed in the recommended XT MOPS buffer. Gels were stained with Bio-Safe Coomassie Stain according to the manufacturer's (Bio-Rad) protocol and imaged using the Alpha Innotech Imaging system (San Leandro, Calif.).

Inclusion Body Preparation.

DIG-152 protein inclusion body (IB) preparations were performed on cells from *P. fluorescens* fermentations that produced insoluble Bt insecticidal protein, as demonstrated by SDS-PAGE and MALDI-MS (Matrix Assisted Laser Desorption/Ionization Mass Spectrometry). *P. fluorescens* fermentation pellets were thawed in a 37° water bath. The cells were resuspended to 25% w/v in lysis buffer [50 mM Tris, pH 7.5, 200 mM NaCl, 20 mM EDTA disodium salt (Ethylenediaminetetraacetic acid), 1% Triton X-100, and 5 mM Dithiothreitol (DTT); 5 mL/L of bacterial protease inhibitor cocktail (Catalog #P8465; Sigma-Aldrich, St. Louis, Mo.) were added just prior to use]. The cells were suspended using a hand-held homogenizer at lowest setting (Tissue Tearor, BioSpec Products, Inc., Bartlesville, Okla.). Lysozyme (25 mg of Sigma L7651, from chicken egg white) was added to the cell suspension by mixing with a metal spatula, and the suspension was incubated at room temperature for one hour. The suspension was cooled on ice for 15 minutes, then sonicated using a Branson Sonifier 250 (two 1-minute sessions, at 50% duty cycle, 30% output). Cell lysis was checked by microscopy. An additional 25 mg of lysozyme were added if necessary, and the incubation and sonication were repeated. Following confirmation of cell lysis via microscopy, the lysate was centrifuged at 11,500×g for 25 minutes (4°) to form the IB pellet, and the supernatant was discarded. The IB pellet was resuspended with 100 mL lysis buffer, homogenized with the hand-held mixer and centrifuged as above. The IB pellet was repeatedly washed by resuspension (in 50 mL lysis buffer), homogenization, sonication, and centrifugation until the supernatant became colorless and the IB pellet became firm and off-white in color. For the final wash, the IB pellet was resuspended in sterile-filtered (0.22 μm) distilled water containing 2 mM EDTA, and centrifuged. The final pellet was resuspended in sterile-filtered distilled water containing 2 mM EDTA, and stored in 1 mL aliquots at −80°.

SDS-PAGE analysis and quantitation of protein in IB preparations was done by thawing a 1 mL aliquot of IB pellet and diluting 1:20 with sterile-filtered distilled water. The diluted sample was then boiled with 4× reducing sample buffer [250 mM Tris, pH6.8, 40% glycerol (v/v), 0.4% Bromophenol Blue (w/v), 8% SDS (w/v) and 8% β-mercaptoethanol (v/v)] and loaded onto a Novex® 4-20% Tris-Glycine, 12+2 well gel (Invitrogen) run with 1× Tris/Glycine/SDS buffer (BioRad). The gel was run for 60 min at 200 volts then stained with Coomassie Blue (50% G-250/50% R-250 in 45% methanol, 10% acetic acid), and destained with 7% acetic acid, 5% methanol in distilled water. Quantification of target bands was done by comparing densitometric values for the bands against Bovine Serum Albumin (BSA) standard samples run on the same gel to generate a standard curve.

Solubilization of Inclusion Bodies.

Six mL of DIG-152 inclusion body suspension from Pf clone DPf108 were centrifuged on the highest setting of an Eppendorf model 5415C microfuge (approximately 14,000×g) to pellet the inclusions. The storage buffer supernatant was removed and replaced with 25 mL of 100 mM sodium carbonate buffer, pH11, in a 50 mL conical tube. Inclusions were resuspended using a pipette and vortexed to mix thoroughly. The tube was placed on a gently rocking platform at 4° overnight to extract the target protein. The extract was centrifuged at 30,000×g for 30 min at 4°, and the resulting supernatant was concentrated 5-fold using an Amicon Ultra-15 regenerated cellulose centrifugal filter device (30,000 Molecular Weight Cutoff; Millipore). The sample buffer was then changed to 10 mM CAPS [3-(cyclohexamino)1-propanesulfonic acid] pH 10 using disposable PD-10 columns (GE Healthcare, Piscataway, N.J.).

Solubilization and Trypsin Activation of Inclusion Body Protein.

In some instances, DIG-152 inclusion body suspension from Pf clone DPf108 was centrifuged on the highest setting of an Eppendorf model 5415C microfuge (approximately 14,000×g) to pellet the inclusions. The storage buffer supernatant was removed and replaced with 100 mM CAPS, pH 11 to provide a protein concentration of approximately 50 mg/mL. The tube was rocked at room temperature for three hours to completely solubilize the protein. Trypsin was added at an amount equal to 5% to 10% (w:w, based on the initial weight of IB powder) and digestion was accomplished by incubation while rocking overnight at 4° or by rocking 90-120 minutes at room temperature. Insoluble material was removed by centrifugation at 10,000×g for 15 minutes, and the supernatant was applied to a MonoQ anion exchange column (10 mm by 10 cm). Activated DIG-152 protein was eluted (as determined by SDS-PAGE, see below) by a 0% to 100% 1 M NaCl gradient over 25 column volumes. Fractions containing the activated protein were pooled and, when necessary, concentrated to less than 10 mL using an Amicon Ultra-15 regenerated cellulose centrifugal filter device as above. The material was then passed through a Superdex 200 column (16 mm by 60 cm) in buffer containing 100 mM NaCl. 10% glycerol, 0.5% Tween-20 and 1 mM EDTA. It was determined by SDS-PAGE analysis that the activated (enzymatically truncated) protein elutes at 65 to 70 mL. Fractions containing the activated protein were pooled and concentrated using the centrifugal concentrator as above.

Gel Electrophoresis.

The concentrated protein preparations were prepared for electrophoresis by diluting 1:50 in NuPAGE® LDS sample buffer (Invitrogen) containing 5 mM DTT as a reducing agent and heated at 95° for 4 minutes. The sample was loaded in duplicate lanes of a 4-12% NuPAGE® gel alongside five BSA standards ranging from 0.2 μg to 2 μg/lane (for standard curve generation). Voltage was applied at 200 V using MOPS SDS running buffer (Invitrogen) until the tracking dye reached the bottom of the gel. The gel was stained with 0.2% Coomassie Blue G-250 in 45% methanol, 10% acetic acid, and destained, first briefly with 45% methanol, 10% acetic acid, and then at length with 7% acetic acid, 5% methanol until the background cleared. Following destaining, the gel was scanned with a BioRad Fluor-S MultiImager. The instrument's Quantity One Software v.4.5.2 was used to obtain background-subtracted volumes of the stained protein bands and to generate the BSA standard curve that was used to calculate the concentration of chimeric DIG-152 protein in the stock solution.

Example 3

Preparation of Cry1Ca and Cry1Ab Core Toxin Proteins and Isolation of *Spodoptera frugiperda* Brush Border Membrane Vesicles for Use in Competitive Binding Experiments The following examples evaluate the competition binding of Cry1 core toxin proteins to putative receptors in insect gut tissues. It is shown that 125I-labeled Cry1Ca core toxin protein binds with high affinity to Brush Border Membrane Vesicles (BBMV's) prepared from *Spodoptera frugiperda* (fall armyworm) and that Cry1Ab core toxin protein does not compete with this binding. In the alternative, it is shown that 125I-labeled Cry1Ab core toxin protein binds with high affinity to BBMV's prepared from *S. frugiperda* and that Cry1Ca core toxin protein does not compete with this binding.

Purification of Cry Proteins.

A gene encoding a chimeric DIG-152 protein, comprising the Cry1Ca3 core toxin and Cry1Ab protoxin, was expressed in the *Pseudomonas fluorescens* expression strain as described in Example 2. In similar fashion, a gene encoding a Cry1Ab protein was expressed in the Pf system. The *P. fluorescens* strain that expresses Cry1Ab protein was named DPf88.

The proteins were purified by the methods of Example 2, and trypsin digestion to produce activated core toxins from the full-length proteins was then performed, and the products were purified by the methods described in Example 2. Preparations of the trypsin processed (activated core toxin) proteins were >95% pure and had a molecular weight of approximately 65 kDa as determined experimentally by SDS-PAGE. As used herein, the activated core toxin prepared from the DIG-152 protein is called the Cry1Ca core toxin protein, and the activated core toxin prepared from the Cry1Ab protein is called the Cry1Ab core toxin protein.

Preparation and Fractionation of Solubilized BBMV's.

Standard methods of protein quantification and SDS-polyacrylamide gel electrophoresis were employed as taught, for example, in Sambrook et al. (1989) and Ausubel et al. (1995), and updates thereof.

Last instar *S. frugiperda* larvae were fasted overnight and then dissected after chilling on ice for 15 minutes. The midgut tissue was removed from the body cavity, leaving behind the hindgut attached to the integument. The midgut was placed in a 9× volume of ice cold homogenization buffer (300 mM mannitol, 5 mM EGTA, 17 mM Tris base, pH7.5), supplemented with Protease Inhibitor Cocktail (Sigma-Aldrich P-2714) diluted as recommended by the supplier. The tissue was homogenized with 15 strokes of a glass tissue homogenizer. BBMV's were prepared by the $MgCl_2$ precipitation method of Wolfersberger (1993). Briefly, an equal volume of a 24 mM $MgCl_2$ solution in 300 mM mannitol was mixed with the midgut homogenate, stirred for 5 minutes and allowed to stand on ice for 15 min. The solution was centrifuged at 2,500×g for 15 min at 4°. The supernatant was saved and the pellet suspended into the original volume of 0.5× diluted homogenization buffer and centrifuged again. The two supernatants were combined and centrifuged at 27,000×g for 30 min at 4° to form the BBMV fraction. The pellet was suspended into BBMV Storage Buffer (10 mM HEPES, 130 mM KCl, 10% glycerol, pH7.4) to a protein concentration of about 3 mg/mL. Protein concentration was determined using Bovine Serum Albumin (BSA) as the standard. Alkaline phosphatase determination (a marker enzyme for the BBMV fraction) was made prior to freezing the samples using the QuantiChrom™ DALP-250 Alkaline Phosphatase Assay Kit (Gentaur Molecular Products, Kampenhout, BE) following the manufacturer's instructions. The specific activity of this enzyme typically increased 7-fold compared to that found in the starting midgut homogenate fraction. The BBMV's were aliquoted into 250 µL samples, flash frozen in liquid nitrogen and stored at −80°.

Electrophoresis.

Analysis of proteins by SDS-PAGE was conducted under reducing (i.e. in 5% β-mercaptoethanol, BME) and denaturing (i.e. heated 5 minutes at 90° in the presence of 2% SDS) conditions. Proteins were loaded into wells of a 4% to 20% Tris-Glycine polyacrylamide gel (BioRad; Hercules, Calif.) and separated at 200 volts for 60 minutes. Protein bands were detected by staining with Coomassie Brilliant Blue R-250 (BioRad) for one hour, and destained with a solution of 5% methanol in 7% acetic acid. The gels were imaged and analyzed using a BioRad Fluoro-S Multi Imager™. Relative molecular weights of the protein bands were determined by comparison to the mobilities of known molecular weight proteins observed in a sample of BenchMark™ Protein Ladder (Life Technologies, Rockville, Md.) loaded into one well of the gel.

Iodination of Cry1Ca or Cry1Ab Core Toxin Proteins.

Purified Cry1Ca core toxin protein or Cry1Ab core toxin protein were iodinated using Pierce Iodination Beads (Thermo Fisher Scientific, Rockford, Ill.). Briefly, two Iodination Beads were washed twice with 500 µL of PBS (20 mM sodium phosphate, 0.15 M NaCl, pH7.5), and placed into a 1.5 mL centrifuge tube with 100 µL of PBS. 0.5 mCi of 125I-labeled sodium iodide was added, the components were allowed to react for 5 minutes at room temperature, then 1 µg of Cry1Ca core toxin protein (or 1 µg of Cry1Ab core toxin protein) was added to the solution and allowed to react for an additional 3 to 5 minutes. The reaction was terminated by pipetting the solution from the Iodination Beads and applying it to a Zeba™ spin column (Invitrogen) equilibrated in 50 mM CAPS, pH10.0, 1 mM DTT (dithiothreitol), 1 mM EDTA, and 5% glycerol. The Iodination Beads were washed twice with 10 µL of PBS and the wash solution was also applied to the Zeba™ desalting column. The radioactive solution was eluted through the spin column by centrifuging at 1,000×g for 2 min. 125I-radiolabeled Cry1Ca core toxin protein (or Cry1Ab core toxin protein) was then dialyzed against 50 mM CAPS, pH10.0, 1 mM DTT, 1 mM EDTA, and 5% glycerol.

Imaging.

Radio-purity of the iodinated Cry1Ca or Cry1Ab core toxin proteins was determined by SDS-PAGE and phosphorimaging. Briefly, SDS-PAGE gels were dried using a BioRad gel drying apparatus following the manufacturer's instructions. The dried gels were imaged by wrapping them in Mylar film (12 µm thick) and exposing them under a Molecular Dynamics storage phosphor screen (35 cm×43 cm) for 1 hour. The plates were developed using a Molecular Dynamics Storm 820 phosphorimager and the image was analyzed using ImageQuant™ software.

Example 4

Binding of 125I-Labeled Cry1 Core Toxin Protein to BBMV's from *Spodoptera frugiperda*

A saturation curve was generated to determine the optimal amount of BBMV protein to use in the binding assays with Cry1Ca and Cry1Ab core toxin proteins. 0.5 nM of 125I-radiolabeled Cry1 core toxin protein was incubated for 1 hr at 28° in binding buffer (8 mM $NaHPO_4$, 2 mM $KH_2PO_4$, 150 mM NaCl, 0.1% BSA, pH7.4) with amounts of BBMV protein ranging from 0 µg/mL to 500 µg/mL (total volume of 0.5 mL). 125I-labeled Cry1 core toxin protein bound to the BBMV proteins was separated from the unbound fraction by sampling 150 µL of the reaction mixture in triplicate into separate 1.5 mL centrifuge tubes and centrifuging the samples at 14,000×g for 8 minutes at room temperature. The supernatant was gently removed and the pellet was washed three times with ice cold binding buffer. The bottom of the centrifuge tube containing the pellet was cut off, placed into a 13×75 mm glass culture tube and the samples were counted for 5 minutes each in the gamma counter. CPM (counts per minute) obtained minus background CPM (reaction with no BBMV protein) was plotted versus BBMV protein concentration. In accordance with results reported by others (Luo et al. 1999), the optimal concentration of BBMV protein to use in the binding assays was determined to be 150 µg/mL.

Example 5

Competitive Binding Assays to BBMVs from *S. frugiperda* with Core Toxin Proteins of Cry1Ab and Cry1Ca Homologous and heterologous competition binding assays were conducted using 150 µg/mL of *S. frugiperda* BBMV protein and 0.5 nM of the 125I-radiolabeled Cry1Ca core toxin protein. Concentrations of the competitive non-radiolabeled Cry1Ab core toxin protein added to the reaction mixture ranged from 0.045 nM to 300 nM and were added at the same time as the radioactive Cry1Ca core toxin protein, to assure true binding competition. Incubations were carried out for 1 hr at 28° and the amount of 125I-labeled Cry1Ca core toxin protein bound to the BBMV (specific binding) was measured as described above. Non-specific binding was represented by the counts obtained in the presence of 1,000 nM of non-radiolabeled Cry1Ca core toxin protein. One hundred percent total binding was considered to be the amount of binding in the absence of any competitor Cry1Ab core toxin protein.

Receptor binding assays using 125I-labeled Cry1Ca core toxin protein determined the ability of the Cry1Ab core toxin protein to displace this radiolabeled ligand from its binding site on BBMV's from *S. frugiperda*. The results (FIG. 1) show that the Cry1Ab core toxin protein did not displace bound 125I-labeled Cry1Ca core toxin protein from its receptor protein(s) at concentrations as high as 300 nM (600 times the concentration of the radioactive binding ligand). As expected, unlabeled Cry1Ca core toxin protein was able to displace radiolabeled Cry1Ca core toxin protein from its binding protein(s), exhibiting a sigmoidal dose response curve with 50% displacement occurring at 5 nM.

It is thus indicated that the Cry1Ca core toxin protein interacts with a binding site in *S. frugiperda* BBMVs that does not bind the Cry1Ab core toxin protein.

Example 6

Competitive Binding Assays to BBMVs from *S. frugiperda* with Core Toxin Proteins of Cry1Ca and Cry1Ab Homologous and heterologous competition binding assays were conducted using 150 µg/mL BBMV protein and 0.5 nM of the 125I-radiolabeled Cry1Ab core toxin protein. Concentrations of the competitive non-radiolabeled Cry1Ca core toxin protein added to the reaction mixture ranged from 0.045 nM to 1000 nM and were added at the same time as the radioactive Cry1Ab core toxin protein, to assure true binding competition. Incubations were carried out for 1 hr at 28° and the amount of 125I-labeled Cry1Ab core toxin protein bound to the BBMV (specific binding) was measured as described above. Non-specific binding was represented by the counts obtained in the presence of 1000 nM of non-radiolabeled Cry1Ab core toxin protein. One hundred percent total binding was considered to be the amount of binding in the absence of any competitor Cry1Ca core toxin protein.

Receptor binding assays using 125I-labeled Cry1Ab core toxin protein determined the ability of the Cry1Ca core toxin protein to displace this radiolabeled ligand from its binding site on BBMV's from *S. frugiperda*. The results (FIG. 2) show that the Cry1Ca core toxin protein did not displace bound 125I-labeled Cry1Ab core toxin protein from its receptor protein(s) at concentrations as high as 300 nM (600 times the concentration of the radioactive binding ligand). As expected, unlabeled Cry1Ab core toxin protein was able to displace radiolabeled Cry1Ab core toxin protein from its binding protein(s), exhibiting a sigmoidal dose response curve with 50% displacement occurring at 5 nM.

It is thus indicated that the Cry1Ab core toxin protein interacts with a binding site in *S. frugiperda* BBMV that does not bind the Cry1Ca core toxin protein.

REFERENCES

Finney, D. J. 1971. Probit analysis. Cambridge University Press, England.

Hua, G., L. Masson, J. L. Jurat-Fuentes, G. Schwab, and M. J. Adang. Binding analyses of *Bacillus thuringiensis* Cry d-endotoxins using brush border membrane vesicles of *Ostrinia nubilalis*. Applied and Environmental Microbiology 67[2], 872-879. 2001.

LeOra Software. 1987. POLO-PC. A user's guide to probit and logit analysis. Berkeley, Calif.

McGaughey, W. H., F. Gould, and W. Gelernter. Bt resistance management. Nature Biotechnology 16[2], 144-146. 1998

Marton, P. R. G. C., L. J. Young, K. Steffey, and B. D. Siegfried. 1999. Baseline susceptibility of the European corn borer, *Ostrinia nubilalis* (Hübner) (Lepidoptera: Pyralidae) to *Bacillus thuringiensis* toxins. J. Econ. Entomol. 92 (2): 280-285.

Robertson, L. J. and H. K. Preisler. 1992. Pesticide bioassays with arthropods. CRC Press, Boca Ranton, Fla.

SAS Institute Inc. 1988. SAS procedures guide, Release 6.03 edition. SAS Institute Inc, Cary, N.C.

Stone, B. F. 1968. A formula for determining degree of dominance in cases of monofactorial inheritance of resistance to chemicals. Bull. WHO 38:325-329.

Van Mellaert, H., J. Botterman, J. Van Rie, and H. Joos. Transgenic plants for the prevention of development of insects resistant to *Bacillus thuringiensis* toxins. (Plant Genetic Systems N.V., Belg. 89-401499[400246], 57-19901205. EP. May 31, 1989

APPENDIX A

List of delta-endotoxins—from Crickmore et al. website (cited in application)
Accession Number is to NCBI entry (if available)

| Name | Acc No. | Authors | Year | Source Strain | Comment |
|---|---|---|---|---|---|
| Cry1Aa1 | AAA22353 | Schnepf et al | 1985 | Bt kurstaki HD1 | |
| Cry1Aa2 | AAA22552 | Shibano et al | 1985 | Bt sotto | |
| Cry1Aa3 | BAA00257 | Shimizu et al | 1988 | Bt aizawai IPL7 | |
| Cry1Aa4 | CAA31886 | Masson et al | 1989 | Bt entomocidus | |
| Cry1Aa5 | BAA04468 | Udayasuriyan et al | 1994 | Bt Fu-2-7 | |
| Cry1Aa6 | AAA86265 | Masson et al | 1994 | Bt kurstaki NRD-12 | |
| Cry1Aa7 | AAD46139 | Osman et al | 1999 | Bt C12 | |
| Cry1Aa8 | I26149 | Liu | 1996 | | DNA sequence only |
| Cry1Aa9 | BAA77213 | Nagamatsu et al | 1999 | Bt dendrolimus T84A1 | |
| Cry1Aa10 | AAD55382 | Hou and Chen | 1999 | Bt kurstaki HD-1-02 | |
| Cry1Aa11 | CAA70856 | Tounsi et al | 1999 | Bt kurstaki | |
| Cry1Aa12 | AAP80146 | Yao et al | 2001 | Bt Ly30 | |
| Cry1Aa13 | AAM44305 | Zhong et al | 2002 | Bt sotto | |
| Cry1Aa14 | AAP40639 | Ren et al | 2002 | unpublished | |
| Cry1Aa15 | AAY66993 | Sauka et al | 2005 | Bt INTA Mol-12 | |
| Cry1Ab1 | AAA22330 | Wabiko et al | 1986 | Bt berliner 1715 | |
| Cry1Ab2 | AAA22613 | Thorne et al | 1986 | Bt kurstaki | |
| Cry1Ab3 | AAA22561 | Geiser et al | 1986 | Bt kurstaki HD1 | |
| Cry1Ab4 | BAA00071 | Kondo et al | 1987 | Bt kurstaki HD1 | |
| Cry1Ab5 | CAA28405 | Hofte et al | 1986 | Bt berliner 1715 | |
| Cry1Ab6 | AAA22420 | Hefford et al | 1987 | Bt kurstaki NRD-12 | |
| Cry1Ab7 | CAA31620 | Haider & Ellar | 1988 | Bt aizawai IC1 | |
| Cry1Ab8 | AAA22551 | Oeda et al | 1987 | Bt aizawai IPL7 | |
| Cry1Ab9 | CAA38701 | Chak & Jen | 1993 | Bt aizawai HD133 | |
| Cry1Ab10 | A29125 | Fischhoff et al | 1987 | Bt kurstaki HD1 | |
| Cry1Ab11 | I12419 | Ely & Tippett | 1995 | Bt A20 | DNA sequence only |
| Cry1Ab12 | AAC64003 | Silva-Werneck et al | 1998 | Bt kurstaki S93 | |
| Cry1Ab13 | AAN76494 | Tan et al | 2002 | Bt c005 | |
| Cry1Ab14 | AAG16877 | Meza-Basso & Theoduloz | 2000 | Native Chilean Bt | |
| Cry1Ab15 | AAO13302 | Li et al | 2001 | Bt B-Hm-16 | |
| Cry1Ab16 | AAK55546 | Yu et al | 2002 | Bt AC-11 | |
| Cry1Ab17 | AAT46415 | Huang et al | 2004 | Bt WB9 | |
| Cry1Ab18 | AAQ88259 | Stobdan et al | 2004 | Bt | |
| Cry1Ab19 | AAW31761 | Zhong et al | 2005 | Bt X-2 | |
| Cry1Ab20 | ABB72460 | Liu et al | 2006 | BtC008 | |
| Cry1Ab21 | ABS18384 | Swiecicka et al | 2007 | Bt IS5056 | |
| Cry1Ab22 | ABW87320 | Wu and Feng | 2008 | BtS2491Ab | |
| Cry1Ab-like | AAK14336 | Nagarathinam et al | 2001 | Bt kunthala RX24 | uncertain sequence |
| Cry1Ab-like | AAK14337 | Nagarathinam et al | 2001 | Bt kunthala RX28 | uncertain sequence |
| Cry1Ab-like | AAK14338 | Nagarathinam et al | 2001 | Bt kunthala RX27 | uncertain sequence |
| Cry1Ab-like | ABG88858 | Lin et al | 2006 | Bt ly4a3 | insufficient sequence |
| Cry1Ac1 | AAA22331 | Adang et al | 1985 | Bt kurstaki HD73 | |
| Cry1Ac2 | AAA22338 | Von Tersch et al | 1991 | Bt kenyae | |
| Cry1Ac3 | CAA38098 | Dardenne et al | 1990 | Bt BTS89A | |
| Cry1Ac4 | AAA73077 | Feitelson | 1991 | Bt kurstaki PS85A1 | |
| Cry1Ac5 | AAA22339 | Feitelson | 1992 | Bt kurstaki PS81GG | |
| Cry1Ac6 | AAA86266 | Masson et al | 1994 | Bt kurstaki NRD-12 | |
| Cry1Ac7 | AAB46989 | Herrera et al | 1994 | Bt kurstaki HD73 | |
| Cry1Ac8 | AAC44841 | Omolo et al | 1997 | Bt kurstaki HD73 | |
| Cry1Ac9 | AAB49768 | Gleave et al | 1992 | Bt DSIR732 | |
| Cry1Ac10 | CAA05505 | Sun | 1997 | Bt kurstaki YBT-1520 | |
| Cry1Ac11 | CAA10270 | Makhdoom & Riazuddin | 1998 | | |
| Cry1Ac12 | I12418 | Ely & Tippett | 1995 | Bt A20 | DNA sequence only |
| Cry1Ac13 | AAD38701 | Qiao et al | 1999 | Bt kurstaki HD1 | |
| Cry1Ac14 | AAQ06607 | Yao et al | 2002 | Bt Ly30 | |
| Cry1Ac15 | AAN07788 | Tzeng et al | 2001 | Bt from Taiwan | |
| Cry1Ac16 | AAU87037 | Zhao et al | 2005 | Bt H3 | |
| Cry1Ac17 | AAX18704 | Hire et al | 2005 | Bt kenyae HD549 | |
| Cry1Ac18 | AAY88347 | Kaur & Allam | 2005 | Bt SK-729 | |
| Cry1Ac19 | ABD37053 | Gao et al | 2005 | Bt C-33 | |
| Cry1Ac20 | ABB89046 | Tan et al | 2005 | | |
| Cry1Ac21 | AAY66992 | Sauka et al | 2005 | INTA Mol-12 | |
| Cry1Ac22 | ABZ01836 | Zhang & Fang | 2008 | Bt W015-1 | |
| Cry1Ac23 | CAQ30431 | Kashyap et al | 2008 | Bt | |
| Cry1Ac24 | ABL01535 | Arango et al | 2008 | Bt 146-158-01 | |
| Cry1Ac25 | FJ513324 | Guan Peng et al | 2008 | Bt Tm37-6 | No NCBI link July 2009 |
| Cry1Ac26 | FJ617446 | Guan Peng et al | 2009 | Bt Tm41-4 | No NCBI link July 2009 |
| Cry1Ac27 | FJ617447 | Guan Peng et al | 2009 | Bt Tm44-1B | No NCBI link July 2009 |
| Cry1Ac28 | ACM90319 | Li et al | 2009 | Bt Q-12 | |
| Cry1Ad1 | AAA22340 | Feitelson | 1993 | Bt aizawai PS81I | |
| Cry1Ad2 | CAA01880 | Anonymous | 1995 | Bt PS81RR1 | |
| Cry1Ae1 | AAA22410 | Lee & Aronson | 1991 | Bt alesti | |
| Cry1Af1 | AAB82749 | Kang et al | 1997 | Bt NT0423 | |
| Cry1Ag1 | AAD46137 | Mustafa | 1999 | | |
| Cry1Ah1 | AAQ14326 | Tan et al | 2000 | | |

APPENDIX A-continued

List of delta-endotoxins—from Crickmore et al. website (cited in application)
Accession Number is to NCBI entry (if available)

| Name | Accession | Authors | Year | Source | Notes |
|---|---|---|---|---|---|
| Cry1Ah2 | ABB76664 | Qi et al | 2005 | Bt alesti | |
| Cry1Ai1 | AAO39719 | Wang et al | 2002 | | |
| Cry1A-like | AAK14339 | Nagarathinam et al | 2001 | Bt kunthala nags3 | uncertain sequence |
| Cry1Ba1 | CAA29898 | Brizzard & Whiteley | 1988 | Bt thuringiensis HD2 | |
| Cry1Ba2 | CAA65003 | Soetaert | 1996 | Bt entomocidus HD110 | |
| Cry1Ba3 | AAK63251 | Zhang et al | 2001 | | |
| Cry1Ba4 | AAK51084 | Nathan et al | 2001 | Bt entomocidus HD9 | |
| Cry1Ba5 | ABO20894 | Song et al | 2007 | Bt sfw-12 | |
| Cry1Ba6 | ABL60921 | Martins et al | 2006 | Bt S601 | |
| Cry1Bb1 | AAA22344 | Donovan et al | 1994 | Bt EG5847 | |
| Cry1Bc1 | CAA86568 | Bishop et al | 1994 | Bt morrisoni | |
| Cry1Bd1 | AAD10292 | Kuo et al | 2000 | Bt wuhanensis HD525 | |
| Cry1Bd2 | AAM93496 | Isakova et al | 2002 | Bt 834 | |
| Cry1Be1 | AAC32850 | Payne et al | 1998 | Bt PS158C2 | |
| Cry1Be2 | AAQ52387 | Baum et al | 2003 | | |
| Cry1Be3 | FJ716102 | Xiaodong Sun et al | 2009 | Bt | No NCBI link July 2009 |
| Cry1Bf1 | CAC50778 | Arnaut et al | 2001 | | |
| Cry1Bf2 | AAQ52380 | Baum et al | 2003 | | |
| Cry1Bg1 | AAO39720 | Wang et al | 2002 | | |
| Cry1Ca1 | CAA30396 | Honee et al | 1988 | Bt entomocidus 60.5 | |
| Cry1Ca2 | CAA31951 | Sanchis et al | 1989 | Bt aizawai 7.29 | |
| Cry1Ca3 | AAA22343 | Feitelson | 1993 | Bt aizawai PS81I | |
| Cry1Ca4 | CAA01886 | Van Mellaert et al | 1990 | Bt entomocidus HD110 | |
| Cry1Ca5 | CAA65457 | Strizhov | 1996 | Bt aizawai 7.29 | |
| Cry1Ca6 | AAF37224 | Yu et al | 2000 | Bt AF-2 | |
| Cry1Ca7 | AAG50438 | Aixing et al | 2000 | Bt J8 | |
| Cry1Ca8 | AAM00264 | Chen et al | 2001 | Bt c002 | |
| Cry1Ca9 | AAL79362 | Kao et al | 2003 | Bt G10-01A | |
| Cry1Ca10 | AAN16462 | Lin et al | 2003 | Bt E05-20a | |
| Cry1Ca11 | AAX53094 | Cai et al | 2005 | Bt C-33 | |
| Cry1Cb1 | M97880 | Kalman et al | 1993 | Bt galleriae HD29 | DNA sequence only |
| Cry1Cb2 | AAG35409 | Song et al | 2000 | Bt c001 | |
| Cry1Cb3 | ACD50894 | Huang et al | 2008 | Bt 087 | |
| Cry1Cb-like | AAX63901 | Thammasittirong et al | 2005 | Bt TA476-1 | insufficient sequence |
| Cry1Da1 | CAA38099 | Hofte et al | 1990 | Bt aizawai HD68 | |
| Cry1Da2 | I76415 | Payne & Sick | 1997 | | DNA sequence only |
| Cry1Db1 | CAA80234 | Lambert | 1993 | Bt BTS00349A | |
| Cry1Db2 | AAK48937 | Li et al | 2001 | Bt B-Pr-88 | |
| Cry1Dc1 | ABK35074 | Lertwiriyawong et al | 2006 | Bt JC291 | |
| Cry1Ea1 | CAA37933 | Visser et al | 1990 | Bt kenyae 4F1 | |
| Cry1Ea2 | CAA39609 | Bosse et al | 1990 | Bt kenyae | |
| Cry1Ea3 | AAA22345 | Feitelson | 1991 | Bt kenyae PS81F | |
| Cry1Ea4 | AAD04732 | Barboza-Corona et al | 1998 | Bt kenyae LBIT-147 | |
| Cry1Ea5 | A15535 | Botterman et al | 1994 | | DNA sequence only |
| Cry1Ea6 | AAL50330 | Sun et al | 1999 | Bt YBT-032 | |
| Cry1Ea7 | AAW72936 | Huehne et al | 2005 | Bt JC190 | |
| Cry1Ea8 | ABX11258 | Huang et al | 2007 | Bt HZM2 | |
| Cry1Eb1 | AAA22346 | Feitelson | 1993 | Bt aizawai PS81A2 | |
| Cry1Fa1 | AAA22348 | Chambers et al | 1991 | Bt aizawai EG6346 | |
| Cry1Fa2 | AAA22347 | Feitelson | 1993 | Bt aizawai PS81I | |
| Cry1Fb1 | CAA80235 | Lambert | 1993 | Bt BTS00349A | |
| Cry1Fb2 | BAA25298 | Masuda & Asano | 1998 | Bt morrisoni INA67 | |
| Cry1Fb3 | AAF21767 | Song et al | 1998 | Bt morrisoni | |
| Cry1Fb4 | AAC10641 | Payne et al | 1997 | | |
| Cry1Fb5 | AAO13295 | Li et al | 2001 | Bt B-Pr-88 | |
| Cry1Fb6 | ACD50892 | Huang et al | 2008 | Bt 012 | |
| Cry1Fb7 | ACD50893 | Huang et al | 2008 | Bt 087 | |
| Cry1Ga1 | CAA80233 | Lambert | 1993 | Bt BTS0349A | |
| Cry1Ga2 | CAA70506 | Shevelev et al | 1997 | Bt wuhanensis | |
| Cry1Gb1 | AAD10291 | Kuo & Chak | 1999 | Bt wuhanensis HD525 | |
| Cry1Gb2 | AAO13756 | Li et al | 2000 | Bt B-Pr-88 | |
| Cry1Gc | AAQ52381 | Baum et al | 2003 | | |
| Cry1Ha1 | CAA80236 | Lambert | 1993 | Bt BTS02069AA | |
| Cry1Hb1 | AAA79694 | Koo et al | 1995 | Bt morrisoni BF190 | |
| Cry1H-like | AAF01213 | Srifah et al | 1999 | Bt JC291 | insufficient sequence |
| Cry1Ia1 | CAA44633 | Tailor et al | 1992 | Bt kurstaki | |
| Cry1Ia2 | AAA22354 | Gleave et al | 1993 | Bt kurstaki | |
| Cry1Ia3 | AAC36999 | Shin et al | 1995 | Bt kurstaki HD1 | |
| Cry1Ia4 | AAB00958 | Kostichka et al | 1996 | Bt AB88 | |
| Cry1Ia5 | CAA70124 | Selvapandiyan | 1996 | Bt 61 | |
| Cry1Ia6 | AAC26910 | Zhong et al | 1998 | Bt kurstaki S101 | |
| Cry1Ia7 | AAM73516 | Porcar et al | 2000 | Bt | |
| Cry1Ia8 | AAK66742 | Song et al | 2001 | | |
| Cry1Ia9 | AAQ08616 | Yao et al | 2002 | Bt Ly30 | |
| Cry1Ia10 | AAP86782 | Espindola et al | 2003 | Bt thuringiensis | |
| Cry1Ia11 | CAC85964 | Tounsi et al | 2003 | Bt kurstaki BNS3 | |
| Cry1Ia12 | AAV53390 | Grossi de Sa et al | 2005 | Bt | |

APPENDIX A-continued

List of delta-endotoxins—from Crickmore et al. website (cited in application)
Accession Number is to NCBI entry (if available)

| | | | | | |
|---|---|---|---|---|---|
| Cry1Ia13 | ABF83202 | Martins et al | 2006 | Bt | |
| Cry1Ia14 | ACG63871 | Liu & Guo | 2008 | Bt11 | |
| Cry1Ia15 | FJ617445 | Guan Peng et al | 2009 | Bt E-1B | No NCBI link July 2009 |
| Cry1Ia16 | FJ617448 | Guan Peng et al | 2009 | Bt E-1A | No NCBI link July 2009 |
| Cry1Ib1 | AAA82114 | Shin et al | 1995 | Bt entomocidus BP465 | |
| Cry1Ib2 | ABW88019 | Guan et al | 2007 | Bt PP61 | |
| Cry1Ib3 | ACD75515 | Liu & Guo | 2008 | Bt GS8 | |
| Cry1Ic1 | AAC62933 | Osman et al | 1998 | Bt C18 | |
| Cry1Ic2 | AAE71691 | Osman et al | 2001 | | |
| Cry1Id1 | AAD44366 | Choi | 2000 | | |
| Cry1Ie1 | AAG43526 | Song et al | 2000 | Bt BTC007 | |
| Cry1If1 | AAQ52382 | Baum et al | 2003 | | |
| Cry1I-like | AAC31094 | Payne et al | 1998 | | insufficient sequence |
| Cry1I-like | ABG88859 | Lin & Fang | 2006 | Bt ly4a3 | insufficient sequence |
| Cry1Ja1 | AAA22341 | Donovan | 1994 | Bt EG5847 | |
| Cry1Jb1 | AAA98959 | Von Tersch & Gonzalez | 1994 | Bt EG5092 | |
| Cry1Jc1 | AAC31092 | Payne et al | 1998 | | |
| Cry1Jc2 | AAQ52372 | Baum et al | 2003 | | |
| Cry1Jd1 | CAC50779 | Arnaut et al | 2001 | Bt | |
| Cry1Ka1 | AAB00376 | Koo et al | 1995 | Bt morrisoni BF190 | |
| Cry1La1 | AAS60191 | Je et al | 2004 | Bt kurstaki K1 | |
| Cry1-like | AAC31091 | Payne et al | 1998 | | insufficient sequence |
| Cry2Aa1 | AAA22335 | Donovan et al | 1989 | Bt kurstaki | |
| Cry2Aa2 | AAA83516 | Widner & Whiteley | 1989 | Bt kurstaki HD1 | |
| Cry2Aa3 | D86064 | Sasaki et al | 1997 | Bt sotto | DNA sequence only |
| Cry2Aa4 | AAC04867 | Misra et al | 1998 | Bt kenyae HD549 | |
| Cry2Aa5 | CAA10671 | Yu & Pang | 1999 | Bt SL39 | |
| Cry2Aa6 | CAA10672 | Yu & Pang | 1999 | Bt YZ71 | |
| Cry2Aa7 | CAA10670 | Yu & Pang | 1999 | Bt CY29 | |
| Cry2Aa8 | AAO13734 | Wei et al | 2000 | Bt Dongbei 66 | |
| Cry2Aa9 | AAO13750 | Zhang et al | 2000 | | |
| Cry2Aa10 | AAQ04263 | Yao et al | 2001 | | |
| Cry2Aa11 | AAQ52384 | Baum et al | 2003 | | |
| Cry2Aa12 | ABI83671 | Tan et al | 2006 | Bt Rpp39 | |
| Cry2Aa13 | ABL01536 | Arango et al | 2008 | Bt 146-158-01 | |
| Cry2Aa14 | ACF04939 | Hire et al | 2008 | Bt HD-550 | |
| Cry2Ab1 | AAA22342 | Widner & Whiteley | 1989 | Bt kurstaki HD1 | |
| Cry2Ab2 | CAA39075 | Dankocsik et al | 1990 | Bt kurstaki HD1 | |
| Cry2Ab3 | AAG36762 | Chen et al | 1999 | Bt BTC002 | |
| Cry2Ab4 | AAO13296 | Li et al | 2001 | Bt B-Pr-88 | |
| Cry2Ab5 | AAQ04609 | Yao et al | 2001 | Bt ly30 | |
| Cry2Ab6 | AAP59457 | Wang et al | 2003 | Bt WZ-7 | |
| Cry2Ab7 | AAZ66347 | Udayasuriyan et al | 2005 | Bt 14-1 | |
| Cry2Ab8 | ABC95996 | Huang et al | 2006 | Bt WB2 | |
| Cry2Ab9 | ABC74968 | Zhang et al | 2005 | Bt LLB6 | |
| Cry2Ab10 | EF157306 | Lin et al | 2006 | Bt LyD | |
| Cry2Ab11 | CAM84575 | Saleem et al | 2007 | Bt CMBL-BT1 | |
| Cry2Ab12 | ABM21764 | Lin et al | 2007 | Bt LyD | |
| Cry2Ab13 | ACG76120 | Zhu et al | 2008 | Bt ywc5-4 | |
| Cry2Ab14 | ACG76121 | Zhu et al | 2008 | Bt Bts | |
| Cry2Ac1 | CAA40536 | Aronson | 1991 | Bt shanghai S1 | |
| Cry2Ac2 | AAG35410 | Song et al | 2000 | | |
| Cry2Ac3 | AAQ52385 | Baum et al | 2003 | | |
| Cry2Ac4 | ABC95997 | Huang et al | 2006 | Bt WB9 | |
| Cry2Ac5 | ABC74969 | Zhang et al | 2005 | | |
| Cry2Ac6 | ABC74793 | Xia et al | 2006 | Bt wuhanensis | |
| Cry2Ac7 | CAL18690 | Saleem et al | 2008 | Bt SBSBT-1 | |
| Cry2Ac8 | CAM09325 | Saleem et al | 2007 | Bt CMBL-BT1 | |
| Cry2Ac9 | CAM09326 | Saleem et al | 2007 | Bt CMBL-BT2 | |
| Cry2Ac10 | ABN15104 | Bai et al | 2007 | Bt QCL-1 | |
| Cry2Ac11 | CAM83895 | Saleem et al | 2007 | Bt HD29 | |
| Cry2Ac12 | CAM83896 | Saleem et al | 2007 | Bt CMBL-BT3 | |
| Cry2Ad1 | AAF09583 | Choi et al | 1999 | Bt BR30 | |
| Cry2Ad2 | ABC86927 | Huang et al | 2006 | Bt WB10 | |
| Cry2Ad3 | CAK29504 | Saleem et al | 2006 | Bt 5_2AcT(1) | |
| Cry2Ad4 | CAM32331 | Saleem et al | 2007 | Bt CMBL-BT2 | |
| Cry2Ad5 | CAO78739 | Saleem et al | 2007 | Bt HD29 | |
| Cry2Ae1 | AAQ52362 | Baum et al | 2003 | | |
| Cry2Af1 | ABO30519 | Beard et al | 2007 | Bt C81 | |
| Cry2Ag | ACH91610 | Zhu et al | 2008 | Bt JF19-2 | |
| Cry2Ah | EU939453 | Zhang et al | 2008 | Bt | No NCBI link July 2009 |
| Cry2Ah2 | ACL80665 | Zhang et al | 2009 | Bt BRC-ZQL3 | |
| Cry2Ai | FJ788388 | Udayasuriyan et al | 2009 | Bt | No NCBI link July 2009 |
| Cry3Aa1 | AAA22336 | Herrnstadt et al | 1987 | Bt san diego | |
| Cry3Aa2 | AAA22541 | Sekar et al | 1987 | Bt tenebrionis | |
| Cry3Aa3 | CAA68482 | Hofte et al | 1987 | | |
| Cry3Aa4 | AAA22542 | McPherson et al | 1988 | Bt tenebrionis | |

APPENDIX A-continued

List of delta-endotoxins—from Crickmore et al. website (cited in application)
Accession Number is to NCBI entry (if available)

| Name | Accession | Authors | Year | Strain | Notes |
|---|---|---|---|---|---|
| Cry3Aa5 | AAA50255 | Donovan et al | 1988 | Bt morrisoni EG2158 | |
| Cry3Aa6 | AAC43266 | Adams et al | 1994 | Bt tenebrionis | |
| Cry3Aa7 | CAB41411 | Zhang et al | 1999 | Bt 22 | |
| Cry3Aa8 | AAS79487 | Gao and Cai | 2004 | Bt YM-03 | |
| Cry3Aa9 | AAW05659 | Bulla and Candas | 2004 | Bt UTD-001 | |
| Cry3Aa10 | AAU29411 | Chen et al | 2004 | Bt 886 | |
| Cry3Aa11 | AAW82872 | Kurt et al | 2005 | Bt tenebrionis Mm2 | |
| Cry3Aa12 | ABY49136 | Sezen et al | 2008 | Bt tenebrionis | |
| Cry3Ba1 | CAA34983 | Sick et al | 1990 | Bt tolworthi 43F | |
| Cry3Ba2 | CAA00645 | Peferoen et al | 1990 | Bt PGSI208 | |
| Cry3Bb1 | AAA22334 | Donovan et al | 1992 | Bt EG4961 | |
| Cry3Bb2 | AAA74198 | Donovan et al | 1995 | Bt EG5144 | |
| Cry3Bb3 | I15475 | Peferoen et al | 1995 | | DNA sequence only |
| Cry3Ca1 | CAA42469 | Lambert et al | 1992 | Bt kurstaki BtI109P | |
| Cry4Aa1 | CAA68485 | Ward & Ellar | 1987 | Bt israelensis | |
| Cry4Aa2 | BAA00179 | Sen et al | 1988 | Bt israelensis HD522 | |
| Cry4Aa3 | CAD30148 | Berry et al | 2002 | Bt israelensis | |
| Cry4A-like | AAY96321 | Mahalakshmi et al | 2005 | Bt LDC-9 | insufficient sequence |
| Cry4Ba1 | CAA30312 | Chungjatpornchai et al | 1988 | Bt israelensis 4Q2-72 | |
| Cry4Ba2 | CAA30114 | Tungpradubkul et al | 1988 | Bt israelensis | |
| Cry4Ba3 | AAA22337 | Yamamoto et al | 1988 | Bt israelensis | |
| Cry4Ba4 | BAA00178 | Sen et al | 1988 | Bt israelensis HD522 | |
| Cry4Ba5 | CAD30095 | Berry et al | 2002 | Bt israelensis | |
| Cry4Ba-like | ABC47686 | Mahalakshmi et al | 2005 | Bt LDC-9 | insufficient sequence |
| Cry4Ca1 | EU646202 | Shu et al | 2008 | | No NCBI link July 2009 |
| Cry4Cb1 | FJ403208 | Jun & Furong | 2008 | Bt HS18-1 | No NCBI link July 2009 |
| Cry4Cb2 | FJ597622 | Jun & Furong | 2008 | BT Ywc2-8 | No NCBI link July 2009 |
| Cry4Cc1 | FJ403207 | Jun & Furong | 2008 | Bt MC28 | No NCBI link July 2009 |
| Cry5Aa1 | AAA67694 | Narva et al | 1994 | Bt darmstadiensis PS17 | |
| Cry5Ab1 | AAA67693 | Narva et al | 1991 | Bt darmstadiensis PS17 | |
| Cry5Ac1 | I34543 | Payne et al | 1997 | | DNA sequence only |
| Cry5Ad1 | ABQ82087 | Lenane et al | 2007 | Bt L366 | |
| Cry5Ba1 | AAA68598 | Foncerrada & Narva | 1997 | Bt PS86Q3 | |
| Cry5Ba2 | ABW88932 | Guo et al | 2008 | YBT 1518 | |
| Cry6Aa1 | AAA22357 | Narva et al | 1993 | Bt PS52A1 | |
| Cry6Aa2 | AAM46849 | Bai et al | 2001 | YBT 1518 | |
| Cry6Aa3 | ABH03377 | Jia et al | 2006 | Bt 96418 | |
| Cry6Ba1 | AAA22358 | Narva et al | 1991 | Bt PS69D1 | |
| Cry7Aa1 | AAA22351 | Lambert et al | 1992 | Bt galleriae PGSI245 | |
| Cry7Ab1 | AAA21120 | Narva & Fu | 1994 | Bt dakota HD511 | |
| Cry7Ab2 | AAA21121 | Narva & Fu | 1994 | Bt kumamotoensis 867 | |
| Cry7Ab3 | ABX24522 | Song et al | 2008 | Bt WZ-9 | |
| Cry7Ab4 | EU380678 | Shu et al | 2008 | Bt | No NCBI link July 2009 |
| Cry7Ab5 | ABX79555 | Aguirre-Arzola et al | 2008 | Bt monterrey GM-33 | |
| Cry7Ab6 | ACI44005 | Deng et al | 2008 | Bt HQ122 | |
| Cry7Ab7 | FJ940776 | Wang et al | 2009 | | No NCBI link September 2009 |
| Cry7Ab8 | GU145299 | Feng Jing | 2009 | | No NCBI link November 2009 |
| Cry7Ba1 | ABB70817 | Zhang et al | 2006 | Bt huazhongensis | |
| Cry7Ca1 | ABR67863 | Gao et al | 2007 | Bt BTH-13 | |
| Cry7Da1 | ACQ99547 | Yi et al | 2009 | Bt LH-2 | |
| Cry8Aa1 | AAA21117 | Narva & Fu | 1992 | Bt kumamotoensis | |
| Cry8Ab1 | EU044830 | Cheng et al | 2007 | Bt B-JJX | No NCBI link July 2009 |
| Cry8Ba1 | AAA21118 | Narva & Fu | 1993 | Bt kumamotoensis | |
| Cry8Bb1 | CAD57542 | Abad et al | 2002 | | |
| Cry8Bc1 | CAD57543 | Abad et al | 2002 | | |
| Cry8Ca1 | AAA21119 | Sato et al. | 1995 | Bt japonensis Buibui | |
| Cry8Ca2 | AAR98783 | Shu et al | 2004 | Bt HBF-1 | |
| Cry8Ca3 | EU625349 | Du et al | 2008 | Bt FTL-23 | No NCBI link July 2009 |
| Cry8Da1 | BAC07226 | Asano et al | 2002 | Bt galleriae | |
| Cry8Da2 | BD133574 | Asano et al | 2002 | Bt | DNA sequence only |
| Cry8Da3 | BD133575 | Asano et al | 2002 | Bt | DNA sequence only |
| Cry8Db1 | BAF93483 | Yamaguchi et al | 2007 | Bt BBT2-5 | |
| Cry8Ea1 | AAQ73470 | Fuping et al | 2003 | Bt 185 | |
| Cry8Ea2 | EU047597 | Liu et al | 2007 | Bt B-DLL | No NCBI link July 2009 |
| Cry8Fa1 | AAT48690 | Shu et al | 2004 | Bt 185 | also AAW81032 |
| Cry8Ga1 | AAT46073 | Shu et al | 2004 | Bt HBF-18 | |
| Cry8Ga2 | ABC42043 | Yan et al | 2008 | Bt 145 | |
| Cry8Ga3 | FJ198072 | Xiaodong et al | 2008 | Bt FCD114 | No NCBI link July 2009 |
| Cry8Ha1 | EF465532 | Fuping et al | 2006 | Bt 185 | No NCBI link July 2009 |
| Cry8Ia1 | EU381044 | Yan et al | 2008 | Bt su4 | No NCBI link July 2009 |
| Cry8Ja1 | EU625348 | Du et al | 2008 | Bt FPT-2 | No NCBI link July 2009 |
| Cry8Ka1 | FJ422558 | Quezado et al | 2008 | | No NCBI link July 2009 |
| Cry8Ka2 | ACN87262 | Noguera & Ibarra | 2009 | Bt kenyae | |
| Cry8-like | FJ770571 | Noguera & Ibarra | 2009 | Bt canadensis | DNA sequence only |
| Cry8-like | ABS53003 | Mangena et al | 2007 | Bt | |
| Cry9Aa1 | CAA41122 | Shevelev et al | 1991 | Bt galleriae | |
| Cry9Aa2 | CAA41425 | Gleave et al | 1992 | Bt DSIR517 | |

APPENDIX A-continued

List of delta-endotoxins—from Crickmore et al. website (cited in application)
Accession Number is to NCBI entry (if available)

| Name | Accession | Authors | Year | Strain | Notes |
|---|---|---|---|---|---|
| Cry9Aa3 | GQ249293 | Su et al | 2009 | Bt SC5(D2) | No NCBI link July 2009 |
| Cry9Aa4 | GQ249294 | Su et al | 2009 | Bt T03C001 | No NCBI link July 2009 |
| Cry9Aa like | AAQ52376 | Baum et al | 2003 | | incomplete sequence |
| Cry9Ba1 | CAA52927 | Shevelev et al | 1993 | Bt galleriae | |
| Cry9Bb1 | AAV28716 | Silva-Werneck et al | 2004 | Bt japonensis | |
| Cry9Ca1 | CAA85764 | Lambert et al | 1996 | Bt tolworthi | |
| Cry9Ca2 | AAQ52375 | Baum et al | 2003 | | |
| Cry9Da1 | BAA19948 | Asano | 1997 | Bt japonensis N141 | |
| Cry9Da2 | AAB97923 | Wasano & Ohba | 1998 | Bt japonensis | |
| Cry9Da3 | GQ249295 | Su et al | 2009 | Bt T03B001 | No NCBI link July 2009 |
| Cry9Da4 | GQ249297 | Su et al | 2009 | Bt T03B001 | No NCBI link July 2009 |
| Cry9Db1 | AAX78439 | Flannagan & Abad | 2005 | Bt kurstaki DP1019 | |
| Cry9Ea1 | BAA34908 | Midoh & Oyama | 1998 | Bt aizawai SSK-10 | |
| Cry9Ea2 | AAO12908 | Li et al | 2001 | Bt B-Hm-16 | |
| Cry9Ea3 | ABM21765 | Lin et al | 2006 | Bt lyA | |
| Cry9Ea4 | ACE88267 | Zhu et al | 2008 | Bt ywc5-4 | |
| Cry9Ea5 | ACF04743 | Zhu et al | 2008 | Bts | |
| Cry9Ea6 | ACG63872 | Liu & Guo | 2008 | Bt 11 | |
| Cry9Ea7 | FJ380927 | Sun et al | 2008 | | No NCBI link July 2009 |
| Cry9Ea8 | GQ249292 | Su et al | 2009 | GQ249292 | No NCBI link July 2009 |
| Cry9Eb1 | CAC50780 | Arnaut et al | 2001 | | |
| Cry9Eb2 | GQ249298 | Su et al | 2009 | Bt T03B001 | No NCBI link July 2009 |
| Cry9Ec1 | AAC63366 | Wasano et al | 2003 | Bt galleriae | |
| Cry9Ed1 | AAX78440 | Flannagan & Abad | 2005 | Bt kurstaki DP1019 | |
| Cry9Ee1 | GQ249296 | Su et al | 2009 | Bt T03B001 | No NCBI link August 2009 |
| Cry9-like | AAC63366 | Wasano et al | 1998 | Bt galleriae | insufficient sequence |
| Cry10Aa1 | AAA22614 | Thorne et al | 1986 | Bt israelensis | |
| Cry10Aa2 | E00614 | Aran & Toomasu | 1996 | Bt israelensis ONR-60A | DNA sequence only |
| Cry10Aa3 | CAD30098 | Berry et al | 2002 | Bt israelensis | |
| Cry10A-like | DQ167578 | Mahalakshmi et al | 2006 | Bt LDC-9 | incomplete sequence |
| Cry11Aa1 | AAA22352 | Donovan et al | 1988 | Bt israelensis | |
| Cry11Aa2 | AAA22611 | Adams et al | 1989 | Bt israelensis | |
| Cry11Aa3 | CAD30081 | Berry et al | 2002 | Bt israelensis | |
| Cry11Aa-like | DQ166531 | Mahalakshmi et al | 2007 | Bt LDC-9 | incomplete sequence |
| Cry11Ba1 | CAA60504 | Delecluse et al | 1995 | Bt jegathesan 367 | |
| Cry11Bb1 | AAC97162 | Orduz et al | 1998 | Bt medellin | |
| Cry12Aa1 | AAA22355 | Narva et al | 1991 | Bt PS33F2 | |
| Cry13Aa1 | AAA22356 | Narva et al | 1992 | Bt PS63B | |
| Cry14Aa1 | AAA21516 | Narva et al | 1994 | Bt sotto PS80JJ1 | |
| Cry15Aa1 | AAA22333 | Brown & Whiteley | 1992 | Bt thompsoni | |
| Cry16Aa1 | CAA63860 | Barloy et al | 1996 | Cb malaysia CH18 | |
| Cry17Aa1 | CAA67841 | Barloy et al | 1998 | Cb malaysia CH18 | |
| Cry18Aa1 | CAA67506 | Zhang et al | 1997 | Paenibacillus popilliae | |
| Cry18Ba1 | AAF89667 | Patel et al | 1999 | Paenibacillus popilliae | |
| Cry18Ca1 | AAF89668 | Patel et al | 1999 | Paenibacillus popilliae | |
| Cry19Aa1 | CAA68875 | Rosso & Delecluse | 1996 | Bt jegathesan 367 | |
| Cry19Ba1 | BAA32397 | Hwang et al | 1998 | Bt higo | |
| Cry20Aa1 | AAB93476 | Lee & Gill | 1997 | Bt fukuokaensis | |
| Cry20Ba1 | ACS93601 | Noguera & Ibarra | 2009 | Bt higo LBIT-976 | |
| Cry20-like | GQ144333 | Yi et al | 2009 | Bt Y-5 | DNA sequence only |
| Cry21Aa1 | I32932 | Payne et al | 1996 | | DNA sequence only |
| Cry21Aa2 | I66477 | Feitelson | 1997 | | DNA sequence only |
| Cry21Ba1 | BAC06484 | Sato & Asano | 2002 | Bt roskildiensis | |
| Cry22Aa1 | I34547 | Payne et al | 1997 | | DNA sequence only |
| Cry22Aa2 | CAD43579 | Isaac et al | 2002 | Bt | |
| Cry22Aa3 | ACD93211 | Du et al | 2008 | Bt FZ-4 | |
| Cry22Ab1 | AAK50456 | Baum et al | 2000 | Bt EG4140 | |
| Cry22Ab2 | CAD43577 | Isaac et al | 2002 | Bt | |
| Cry22Ba1 | CAD43578 | Isaac et al | 2002 | Bt | |
| Cry23Aa1 | AAF76375 | Donovan et al | 2000 | Bt | Binary with Cry37Aa1 |
| Cry24Aa1 | AAC61891 | Kawalek and Gill | 1998 | Bt jegathesan | |
| Cry24Ba1 | BAD32657 | Ohgushi et al | 2004 | Bt sotto | |
| Cry24Ca1 | CAJ43600 | Beron & Salerno | 2005 | Bt FCC-41 | |
| Cry25Aa1 | AAC61892 | Kawalek and Gill | 1998 | Bt jegathesan | |
| Cry26Aa1 | AAD25075 | Wojciechowska et al | 1999 | Bt finitimus B-1166 | |
| Cry27Aa1 | BAA82796 | Saitoh | 1999 | Bt higo | |
| Cry28Aa1 | AAD24189 | Wojciechowska et al | 1999 | Bt finitimus B-1161 | |
| Cry28Aa2 | AAG00235 | Moore and Debro | 2000 | Bt finitimus | |
| Cry29Aa1 | CAC80985 | Delecluse et al | 2000 | Bt medellin | |
| Cry30Aa1 | CAC80986 | Delecluse et al | 2000 | Bt medellin | |
| Cry30Ba1 | BAD00052 | Ito et al | 2003 | Bt entomocidus | |
| Cry30Ca1 | BAD67157 | Ohgushi et al | 2004 | Bt sotto | |
| Cry30Ca2 | ACU24781 | Sun and Park | 2009 | Bt jegathesan 367 | |
| Cry30Da1 | EF095955 | Shu et al | 2006 | Bt Y41 | No NCBI link July 2009 |
| Cry30Db1 | BAE80088 | Kishida et al | 2006 | Bt aizawai BUN1-14 | |
| Cry30Ea1 | ACC95445 | Fang et al | 2007 | Bt S2160-1 | |
| Cry30Ea2 | FJ499389 | Jun et al | 2008 | Bt Ywc2-8 | No NCBI link July 2009 |

APPENDIX A-continued

List of delta-endotoxins—from Crickmore et al. website (cited in application)
Accession Number is to NCBI entry (if available)

| | | | | | |
|---|---|---|---|---|---|
| Cry30Fa1 | ACI22625 | Tan et al | 2008 | Bt MC28 | |
| Cry30Ga1 | ACG60020 | Zhu et al | 2008 | Bt HS18-1 | |
| Cry31Aa1 | BAB11757 | Saitoh & Mizuki | 2000 | Bt 84-HS-1-11 | |
| Cry31Aa2 | AAL87458 | Jung and Cote | 2000 | Bt M15 | |
| Cry31Aa3 | BAE79808 | Uemori et al | 2006 | Bt B0195 | |
| Cry31Aa4 | BAF32571 | Yasutake et al | 2006 | Bt 79-25 | |
| Cry31Aa5 | BAF32572 | Yasutake et al | 2006 | Bt 92-10 | |
| Cry31Ab1 | BAE79809 | Uemori et al | 2006 | Bt B0195 | |
| Cry31Ab2 | BAF32570 | Yasutake et al | 2006 | Bt 31-5 | |
| Cry31Ac1 | BAF34368 | Yasutake et al | 2006 | Bt 87-29 | |
| Cry32Aa1 | AAG36711 | Balasubramanian et al | 2001 | Bt yunnanensis | |
| Cry32Ba1 | BAB78601 | Takebe et al | 2001 | Bt | |
| Cry32Ca1 | BAB78602 | Takebe et al | 2001 | Bt | |
| Cry32Da1 | BAB78603 | Takebe et al | 2001 | Bt | |
| Cry33Aa1 | AAL26871 | Kim et al | 2001 | Bt dakota | |
| Cry34Aa1 | AAG50341 | Ellis et al | 2001 | Bt PS80JJ1 | Binary with Cry35Aa1 |
| Cry34Aa2 | AAK64560 | Rupar et al | 2001 | Bt EG5899 | Binary with Cry35Aa2 |
| Cry34Aa3 | AAT29032 | Schnepf et al | 2004 | Bt PS69Q | Binary with Cry35Aa3 |
| Cry34Aa4 | AAT29030 | Schnepf et al | 2004 | Bt PS185GG | Binary with Cry35Aa4 |
| Cry34Ab1 | AAG41671 | Moellenbeck et al | 2001 | Bt PS149B1 | Binary with Cry35Ab1 |
| Cry34Ac1 | AAG50118 | Ellis et al | 2001 | Bt PS167H2 | Binary with Cry35Ac1 |
| Cry34Ac2 | AAK64562 | Rupar et al | 2001 | Bt EG9444 | Binary with Cry35Ab2 |
| Cry34Ac3 | AAT29029 | Schnepf et al | 2004 | Bt KR1369 | Binary with Cry35Ab3 |
| Cry34Ba1 | AAK64565 | Rupar et al | 2001 | Bt EG4851 | Binary with Cry35Ba1 |
| Cry34Ba2 | AAT29033 | Schnepf et al | 2004 | Bt PS201L3 | Binary with Cry35Ba2 |
| Cry34Ba3 | AAT29031 | Schnepf et al | 2004 | Bt PS201HH2 | Binary with Cry35Ba3 |
| Cry35Aa1 | AAG50342 | Ellis et al | 2001 | Bt PS80JJ1 | Binary with Cry34Aa1 |
| Cry35Aa2 | AAK64561 | Rupar et al | 2001 | Bt EG5899 | Binary with Cry34Aa2 |
| Cry35Aa3 | AAT29028 | Schnepf et al | 2004 | Bt PS69Q | Binary with Cry34Aa3 |
| Cry35Aa4 | AAT29025 | Schnepf et al | 2004 | Bt PS185GG | Binary with Cry34Aa4 |
| Cry35Ab1 | AAG41672 | Moellenbeck et al | 2001 | Bt PS149B1 | Binary with Cry34Ab1 |
| Cry35Ab2 | AAK64563 | Rupar et al | 2001 | Bt EG9444 | Binary with Cry34Ac2 |
| Cry35Ab3 | AY536891 AAT29024 | | 2004 | Bt KR1369 | Binary with Cry34Ab3 |
| Cry35Ac1 | AAG50117 | Ellis et al | 2001 | Bt PS167H2 | Binary with Cry34Ac1 |
| Cry35Ba1 | AAK64566 | Rupar et al | 2001 | Bt EG4851 | Binary with Cry34Ba1 |
| Cry35Ba2 | AAT29027 | Schnepf et al | 2004 | Bt PS201L3 | Binary with Cry34Ba2 |
| Cry35Ba3 | AAT29026 | Schnepf et al | 2004 | Bt PS201HH2 | Binary with Cry34Ba3 |
| Cry36Aa1 | AAK64558 | Rupar et al | 2001 | Bt | |
| Cry37Aa1 | AAF76376 | Donovan et al | 2000 | Bt | Binary with Cry23Aa |
| Cry38Aa1 | AAK64559 | Rupar et al | 2000 | Bt | |
| Cry39Aa1 | BAB72016 | Ito et al | 2001 | Bt aizawai | |
| Cry40Aa1 | BAB72018 | Ito et al | 2001 | Bt aizawai | |
| Cry40Ba1 | BAC77648 | Ito et al | 2003 | Bun1-14 | |
| Cry40Ca1 | EU381045 | Shu et al | 2008 | Bt Y41 | No NCBI link July 2009 |
| Cry40Da1 | ACF15199 | Zhang et al | 2008 | Bt S2096-2 | |
| Cry41Aa1 | BAD35157 | Yamashita et al | 2003 | Bt A1462 | |
| Cry41Ab1 | BAD35163 | Yamashita et al | 2003 | Bt A1462 | |
| Cry42Aa1 | BAD35166 | Yamashita et al | 2003 | Bt A1462 | |
| Cry43Aa1 | BAD15301 | Yokoyama and Tanaka | 2003 | P. lentimorbus semadara | |
| Cry43Aa2 | BAD95474 | Nozawa | 2004 | P. popilliae popilliae | |
| Cry43Ba1 | BAD15303 | Yokoyama and Tanaka | 2003 | P. lentimorbus semadara | |
| Cry43-like | BAD15305 | Yokoyama and Tanaka | 2003 | P. lentimorbus semadara | |
| Cry44Aa | BAD08532 | Ito et al | 2004 | Bt entomocidus INA288 | |
| Cry45Aa | BAD22577 | Okumura et al | 2004 | Bt 89-T-34-22 | |
| Cry46Aa | BAC79010 | Ito et al | 2004 | Bt dakota | |
| Cry46Aa2 | BAG68906 | Ishikawa et al | 2008 | Bt A1470 | |
| Cry46Ab | BAD35170 | Yamagiwa et al | 2004 | Bt | |
| Cry47Aa | AAY24695 | Kongsuwan et al | 2005 | Bt CAA890 | |
| Cry48Aa | CAJ18351 | Jones and Berry | 2005 | Bs IAB59 | binary with 49Aa |
| Cry48Aa2 | CAJ86545 | Jones and Berry | 2006 | Bs 47-6B | binary with 49Aa2 |
| Cry48Aa3 | CAJ86546 | Jones and Berry | 2006 | Bs NHA15b | binary with 49Aa3 |
| Cry48Ab | CAJ86548 | Jones and Berry | 2006 | Bs LP1G | binary with 49Ab1 |
| Cry48Ab2 | CAJ86549 | Jones and Berry | 2006 | Bs 2173 | binary with 49Aa4 |
| Cry49Aa | CAH56541 | Jones and Berry | 2005 | Bs IAB59 | binary with 48Aa |
| Cry49Aa2 | CAJ86541 | Jones and Berry | 2006 | Bs 47-6B | binary with 48Aa2 |
| Cry49Aa3 | CAJ86543 | Jones and Berry | 2006 | BsNHA15b | binary with 48Aa3 |
| Cry49Aa4 | CAJ86544 | Jones and Berry | 2006 | Bs 2173 | binary with 48Ab2 |
| Cry49Ab1 | CAJ86542 | Jones and Berry | 2006 | Bs LP1G | binary with 48Ab1 |
| Cry50Aa1 | BAE86999 | Ohgushi et al | 2006 | Bt sotto | |
| Cry51Aa1 | ABI14444 | Meng et al | 2006 | Bt F14-1 | |
| Cry52Aa1 | EF613489 | Song et al | 2007 | Bt Y41 | No NCBI link July 2009 |
| Cry52Ba1 | FJ361760 | Jun et al | 2008 | Bt BM59-2 | No NCBI link July 2009 |
| Cry53Aa1 | EF633476 | Song et al | 2007 | Bt Y41 | No NCBI link July 2009 |
| Cry53Ab1 | FJ361759 | Jun et al | 2008 | Bt MC28 | No NCBI link July 2009 |
| Cry54Aa1 | ACA52194 | Tan et al | 2009 | Bt MC28 | |
| Cry55Aa1 | ABW88932 | Guo et al | 2008 | YBT 1518 | |
| Cry55Aa2 | AAE33526 | Bradfisch et al | 2000 | BT Y41 | |

APPENDIX A-continued

List of delta-endotoxins—from Crickmore et al. website (cited in application)
Accession Number is to NCBI entry (if available)

| | | | | | | | |
|---|---|---|---|---|---|---|---|
| Cry56Aa1 | | FJ597621 | Jun & Furong | 2008 | Bt Ywc2-8 | No NCBI link July 2009 | |
| Cry56Aa2 | | GQ483512 | Guan Peng et al | 2009 | Bt G7-1 | No NCBI link August 2009 | |
| Cry57Aa1 | | ANC87261 | Noguera & Ibarra | 2009 | Bt kim | | |
| Cry58Aa1 | | ANC87260 | Noguera & Ibarra | 2009 | Bt entomocidus | | |
| Cry59Aa1 | | ACR43758 | Noguera & Ibarra | 2009 | Bt kim LBIT-980 | | |
| Vip3Aa1 | Vip3Aa | AAC37036 | Estruch et al | 1996 | PNAS 93, 5389-5394 | AB88 | |
| Vip3Aa2 | Vip3Ab | AAC37037 | Estruch et al | 1996 | PNAS 93, 5389-5394 | AB424 | |
| Vip3Aa3 | Vip3Ac | | Estruch et al | 2000 | U.S. Pat. No. 6,137,033 October 2000 | | |
| Vip3Aa4 | PS36A Sup | AAR81079 | Feitelson et al | 1998 | U.S. Pat. No. 6,656,908 December 2003 | Bt PS36A | WO9818932(A2, A3) 7 May 1998 |
| Vip3Aa5 | PS81F Sup | AAR81080 | Feitelson et al | 1998 | U.S. Pat. No. 6,656,908 December 2003 | Bt PS81F | WO9818932(A2, A3) 7 May 1998 |
| Vip3Aa6 | Jav90 Sup | AAR81081 | Feitelson et al | 1998 | U.S. Pat. No. 6,656,908 December 2003 | Bt | WO9818932(A2, A3) 7 May 1998 |
| Vip3Aa7 | Vip83 | AAK95326 | Cai et al | 2001 | unpublished | Bt YBT-833 | |
| Vip3Aa8 | Vip3A | AAK97481 | Loguercio et al | 2001 | unpublished | Bt HD125 | |
| Vip3Aa9 | VipS | CAA76665 | Selvapandiyan et al | 2001 | unpublished | Bt A13 | |
| Vip3Aa10 | Vip3V | AAN60738 | Doss et al | 2002 | Protein Expr. Purif. 26, 82-88 | Bt | |
| Vip3Aa11 | Vip3A | AAR36859 | Liu et al | 2003 | unpublished | Bt C9 | |
| Vip3Aa12 | Vip3A-WB5 | AAM22456 | Wu and Guan | 2003 | unpublished | Bt | |
| Vip3Aa13 | Vip3A | AAL69542 | Chen et al | 2002 | Sheng Wu Gong Cheng Xue Bao 18, 687-692 | Bt S184 | |
| Vip3Aa14 | Vip | AAQ12340 | Polumetla et al | 2003 | unpublished | Bt tolworthi | |
| Vip3Aa15 | Vip3A | AAP51131 | Wu et al | 2004 | unpublished | Bt WB50 | |
| Vip3Aa16 | Vip3LB | AAW65132 | Mesrati et al | 2005 | FEMS Micro Lett 244, 353-358 | Bt | |
| Vip3Aa17 | Jav90 | | Feitelson et al | 1999 | U.S. Pat. No. 6,603,063 August 2003 | Javelin 1990 | WO9957282(A2, A3) 11 Nov. 1999 |
| Vip3Aa18 | | AAX49395 | Cai and Xiao | 2005 | unpublished | Bt 9816C | |
| Vip3Aa19 | Vip3ALD | DQ241674 | Liu et al | 2006 | unpublished | Bt AL | |
| Vip3Aa19 | Vip3A-1 | DQ539887 | Hart et al | 2006 | unpublished | | |
| Vip3Aa20 | Vip3A-2 | DQ539888 | Hart et al | 2006 | unpublished | | |
| Vip3Aa21 | Vip | ABD84410 | Panbangred | 2006 | unpublished | Bt aizawai | |
| Vip3Aa22 | Vip3A-LS1 | AAY41427 | Lu et al | 2005 | unpublished | Bt LS1 | |
| Vip3Aa23 | Vip3A-LS8 | AAY43428 | Lu et al | 2005 | unpublished | Bt LS8 | |
| Vip3Aa24 | | BI 880913 | Song et al | 2007 | unpublished | Bt WZ-7 | |
| Vip3Aa25 | | EF608501 | Hsieh et al | 2007 | unpublished | | |
| Vip3Aa26 | | EU294496 | Shen and Guo | 2007 | unpublished | Bt TF9 | |
| Vip3Aa27 | | EU332167 | Shen and Guo | 2007 | unpublished | Bt 16 | |
| Vip3Aa28 | | FJ494817 | Xiumei Yu | 2008 | unpublished | Bt JF23-8 | |
| Vip3Aa29 | | FJ626674 | Xieumei et al | 2009 | unpublished | Bt JF21-1 | |
| Vip3Aa30 | | FJ626675 | Xieumei et al | 2009 | unpublished | MD2-1 | |
| Vip3Aa31 | | FJ626676 | Xieumei et al | 2009 | unpublished | JF21-1 | |
| Vip3Aa32 | | FJ626677 | Xieumei et al | 2009 | unpublished | MD2-1 | |
| Vip3Ab1 | Vip3B | AAR40284 | Feitelson et al | 1999 | U.S. Pat. No. 6,603,063 August 2003 | Bt KB59A4-6 | WO9957282(A2, A3) 11 Nov. 1999 |
| Vip3Ab2 | Vip3D | AAY88247 | Feng and Shen | 2006 | unpublished | Bt | |
| Vip3Ac1 | PS49C | | Narva et al | . | US application 20040128716 | | |
| Vip3Ad1 | PS158C2 | | Narva et al | . | US application 20040128716 | | |
| Vip3Ad2 | ISP3B | CAI43276 | Van Rie et al | 2005 | unpublished | Bt | |
| Vip3Ae1 | ISP3C | CAI43277 | Van Rie et al | 2005 | unpublished | Bt | |
| Vip3Af1 | ISP3A | CAI43275 | Van Rie et al | 2005 | unpublished | Bt | |
| Vip3Af2 | Vip3C | ADN08753 | Syngenta | . | WO 03/075655 | | |
| Vip3Ag1 | Vip3B | ADN08758 | Syngenta | . | WO 02/078437 | | |

APPENDIX A-continued

List of delta-endotoxins—from Crickmore et al. website (cited in application)
Accession Number is to NCBI entry (if available)

| | | | | | | |
|---|---|---|---|---|---|---|
| Vip3Ag2 | | FJ556803 | Audtho et al | 2008 | . | Bt |
| Vip3Ah1 | Vip3S | DQ832323 | Li and Shen | 2006 | unpublished | Bt |
| Vip3Ba1 | | AAV70653 | Rang et al | 2004 | unpublished | . |
| Vip3Bb1 | Vip3Z | ADN08760 | Syngenta | . | WO 03/075655 | |
| Vip3Bb2 | | EF439819 | Akhurst et al | 2007 | | |

---

We claim:

1. A transgenic plant comprising DNA encoding a Cry1C insecticidal protein comprising SEQ ID NO:2 and DNA encoding a Cry1Ab insecticidal protein comprising SEQ ID NO:3, wherein said transgenic plant is selected from the group consisting of corn, soybeans, and sugarcane.

2. Seed or part of the plant of claim 1, wherein said seed or part comprises said DNA encoding said Cry1C insecticidal protein and DNA encoding said Cry1Ab insecticidal protein.

3. A population of plants rising transgenic plants of claim 1 and non-Bt refuge plants, wherein said population of plants is planted in a field and wherein said refuge plants comprise less than 40% of all crop plants in said field.

4. The population of plants of claim 3, wherein said refuge plants comprise less than 5% of all crop plants in said field.

5. The population of plants of claim 3, wherein said refuge plants are in blocks or strips.

6. A mixture of seeds comprising refuge seeds from non-Bt refuge plants, and a plurality of seeds of claim 2, wherein said refuge seeds comprise less than 40% of all the seeds in the mixture.

7. The mixture of seeds of claim 6, wherein said refuge seeds comprise less than 5% of all the seeds in the mixture.

8. A method of managing development of resistance to a Cry toxin by *Spodoptera frugiperda* insects, said method comprising planting seeds to produce the population of plants of claim 3.

9. The plant of claim 1, said plant further comprising DNA encoding a Cry1Fa core toxin-containing protein.

10. A population of plants comprising transgenic plants of claim 9 and non-Bt refuge plants, wherein said population of plants is planted in a field and wherein said refuge plants comprise less than about 20% of all crop plants in said field.

11. The population of plants of claim 10, wherein said field comprises less than about 10% refuge plants.

12. A method of managing development of resistance to a Cry toxin by *Spodoptera frugiperda* insects, said method comprising planting seeds to produce the population field of plants of claim 11.

13. A composition for controlling *Spodoptera* frugiperda insects, said composition comprising cells that express effective amounts of both a Cry1Ab core toxin-containing protein comprising SEQ ID NO:3 and a Cry1C core toxin-containing protein comprising SEQ ID NO:2.

14. The composition of claim 13 comprising a host transformed to express both the Cry1Ab core toxin-containing protein and the Cry1C core toxin containing protein, wherein said host is a microorganism or a plant cell.

15. A method of controlling *Spodoptera frugiperda* insects, said method comprising presenting to said insects or to the environment of said insects an effective amount of the composition of claim 13.

16. The plant of claim 1, wherein said plant is a maize plant.

17. A plant cell of the plant of claim 1, wherein said plant cell comprises said DNA encoding said Cry1C insecticidal protein and said DNA encoding said Cry1Ab insecticidal protein, wherein said Cry1C insecticidal protein comprises SEQ ID NO:2 and said Cry1Ab insecticidal protein comprises SEQ ID NO:3.

18. A plant cell of the plant of claim 9, wherein said plant cell comprises said DNA encoding said Cry1C insecticidal protein and said DNA encoding said Cry1Ab insecticidal protein, wherein said Cry1C insecticidal protein comprises SEQ ID NO:2 and said Cry1Ab insecticidal protein comprises SEQ ID NO:3.

19. A plant cell of the plant of claim 16, wherein said plant cell comprises said DNA encoding said Cry1C insecticidal protein and said DNA encoding said Cry1Ab insecticidal protein, wherein said Cry1C insecticidal protein comprises SEQ ID NO:2 and said Cry1Ab insecticidal protein comprises SEQ ID NO:3.

* * * * *

SEQUENCE LISTING

<160> NUMBER OF SEQ ID NOS: 3

<210> SEQ ID NO 1
<211> LENGTH: 1164
<212> TYPE: PRT
<213> ORGANISM: Artificial Sequence
<220> FEATURE:
<223> OTHER INFORMATION: DIG-152 Chimeric protein

<400> SEQUENCE: 1

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
                20                  25                  30

Asn Ser Ser Ile Asp Ile Ser Leu Ser Leu Val Gln Phe Leu Val Ser
            35                  40                  45

Asn Phe Val Pro Gly Gly Gly Phe Leu Val Gly Leu Ile Asp Phe Val
        50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270
```

```
Ile Asn Phe Asn Pro Gln Leu Gln Ser Val Ala Gln Leu Pro Thr Phe
            275                 280                 285

Asn Val Met Glu Asn Ser Ala Ile Arg Asn Pro His Leu Phe Asp Ile
        290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
            355                 360                 365

Thr Leu Arg Leu Leu Gln Gln Pro Trp Pro Ala Pro Pro Phe Asn Leu
        370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
            435                 440                 445

Val Phe Ser Trp Thr His Arg Ser Ala Thr Leu Thr Asn Thr Ile Asp
        450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
            595                 600                 605

Asp Lys Ile Glu Ile Ile Leu Ala Asp Ala Thr Phe Glu Ala Glu Ser
        610                 615                 620

Asp Leu Glu Arg Ala Gln Lys Ala Val Asn Ala Leu Phe Thr Ser Ser
625                 630                 635                 640

Asn Gln Ile Gly Leu Lys Thr Asp Val Thr Asp Tyr His Ile Asp Arg
                645                 650                 655

Val Ser Asn Leu Val Glu Cys Leu Ser Asp Glu Phe Cys Leu Asp Glu
            660                 665                 670

Lys Lys Glu Leu Ser Glu Lys Val Lys His Ala Lys Arg Leu Ser Asp
            675                 680                 685
```

```
Glu Arg Asn Leu Leu Gln Asp Pro Asn Phe Arg Gly Ile Asn Arg Gln
690                 695                 700

Leu Asp Arg Gly Trp Arg Gly Ser Thr Asp Ile Thr Ile Gln Gly Gly
705                 710                 715                 720

Asp Asp Val Phe Lys Glu Asn Tyr Val Thr Leu Leu Gly Thr Phe Asp
                725                 730                 735

Glu Cys Tyr Pro Thr Tyr Leu Tyr Gln Lys Ile Asp Glu Ser Lys Leu
                740                 745                 750

Lys Ala Tyr Thr Arg Tyr Gln Leu Arg Gly Tyr Ile Glu Asp Ser Gln
            755                 760                 765

Asp Leu Glu Ile Tyr Leu Ile Arg Tyr Asn Ala Lys His Glu Thr Val
770                 775                 780

Asn Val Pro Gly Thr Gly Ser Leu Trp Pro Leu Ser Ala Pro Ser Pro
785                 790                 795                 800

Ile Gly Lys Cys Ala His His Ser His Phe Ser Leu Asp Ile Asp
                805                 810                 815

Val Gly Cys Thr Asp Leu Asn Glu Asp Leu Gly Val Trp Val Ile Phe
        820                 825                 830

Lys Ile Lys Thr Gln Asp Gly His Ala Arg Leu Gly Asn Leu Glu Phe
        835                 840                 845

Leu Glu Glu Lys Pro Leu Val Gly Glu Ala Leu Ala Arg Val Lys Arg
850                 855                 860

Ala Glu Lys Lys Trp Arg Asp Lys Arg Glu Lys Leu Glu Trp Glu Thr
865                 870                 875                 880

Asn Ile Val Tyr Lys Glu Ala Lys Glu Ser Val Asp Ala Leu Phe Val
                885                 890                 895

Asn Ser Gln Tyr Asp Arg Leu Gln Ala Asp Thr Asn Ile Ala Met Ile
                900                 905                 910

His Ala Ala Asp Lys Arg Val His Ser Ile Arg Glu Ala Tyr Leu Pro
            915                 920                 925

Glu Leu Ser Val Ile Pro Gly Val Asn Ala Ala Ile Phe Glu Glu Leu
            930                 935                 940

Glu Gly Arg Ile Phe Thr Ala Phe Ser Leu Tyr Asp Ala Arg Asn Val
945                 950                 955                 960

Ile Lys Asn Gly Asp Phe Asn Asn Gly Leu Ser Cys Trp Asn Val Lys
                965                 970                 975

Gly His Val Asp Val Glu Glu Gln Asn Asn His Arg Ser Val Leu Val
            980                 985                 990

Val Pro Glu Trp Glu Ala Glu Val Ser Gln Glu Val Arg Val Cys Pro
        995                 1000                1005

Gly Arg Gly Tyr Ile Leu Arg Val Thr Ala Tyr Lys Glu Gly Tyr
    1010                1015                1020

Gly Glu Gly Cys Val Thr Ile His Glu Ile Glu Asn Asn Thr Asp
    1025                1030                1035

Glu Leu Lys Phe Ser Asn Cys Val Glu Glu Val Tyr Pro Asn
    1040                1045                1050

Asn Thr Val Thr Cys Asn Asp Tyr Thr Ala Thr Gln Glu Glu Tyr
    1055                1060                1065

Glu Gly Thr Tyr Thr Ser Arg Asn Arg Gly Tyr Asp Gly Ala Tyr
    1070                1075                1080

Glu Ser Asn Ser Ser Val Pro Ala Asp Tyr Ala Ser Ala Tyr Glu
    1085                1090                1095

Glu Lys Ala Tyr Thr Asp Gly Arg Arg Asp Asn Pro Cys Glu Ser
```

```
                    1100                1105                1110

Asn Arg Gly Tyr Gly Asp Tyr Thr Pro Leu Pro Ala Gly Tyr Val
        1115                1120                1125

Thr Lys Glu Leu Glu Tyr Phe Pro Glu Thr Asp Lys Val Trp Ile
    1130                1135                1140

Glu Ile Gly Glu Thr Glu Gly Thr Phe Ile Val Asp Ser Val Glu
    1145                1150                1155

Leu Leu Leu Met Glu Glu
    1160

<210> SEQ ID NO 2
<211> LENGTH: 619
<212> TYPE: PRT
<213> ORGANISM: Artificial Sequence
<220> FEATURE:
<223> OTHER INFORMATION: Cry1Ca

<400> SEQUENCE: 2

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn

```
                290                 295                 300

Leu Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly
                325                 330                 335

Asn Ile Thr Ser Pro Ile Tyr Gly Arg Glu Ala Asn Gln Glu Pro Pro
                340                 345                 350

Arg Ser Phe Thr Phe Asn Gly Pro Val Phe Arg Thr Leu Ser Asn Pro
                355                 360                 365

Thr Leu Arg Leu Leu Gln Gln Pro Trp Pro Ala Pro Pro Phe Asn Leu
                370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
                420                 425                 430

Ala Thr Phe Val Gln Arg Ser Gly Thr Pro Phe Leu Thr Thr Gly Val
                435                 440                 445

Val Phe Ser Trp Thr His Arg Ser Ala Thr Leu Thr Asn Thr Ile Asp
                450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
                500                 505                 510

Asn Ser Pro Ile Thr Gln Arg Tyr Arg Leu Arg Phe Arg Tyr Ala Ser
                515                 520                 525

Ser Arg Asp Ala Arg Val Ile Val Leu Thr Gly Ala Ala Ser Thr Gly
                530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
                580                 585                 590

Gln Pro Leu Phe Gly Ala Gly Ser Ile Ser Ser Gly Glu Leu Tyr Ile
                595                 600                 605

Asp Lys Ile Glu Ile Ile Leu Ala Asp Ala Thr
610                 615

<210> SEQ ID NO 3
<211> LENGTH: 612
<212> TYPE: PRT
<213> ORGANISM: Artificial Sequence
<220> FEATURE:
<223> OTHER INFORMATION: Cry1Ab

<400> SEQUENCE: 3

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
```

-continued

```
                35                  40                  45
Glu Phe Val Pro Gly Ala Gly Phe Val Leu Gly Leu Val Asp Ile Ile
 50                  55                  60
Trp Gly Ile Phe Gly Pro Ser Gln Trp Asp Ala Phe Leu Val Gln Ile
 65                  70                  75                  80
Glu Gln Leu Ile Asn Gln Arg Ile Glu Glu Phe Ala Arg Asn Gln Ala
                 85                  90                  95
Ile Ser Arg Leu Glu Gly Leu Ser Asn Leu Tyr Gln Ile Tyr Ala Glu
            100                 105                 110
Ser Phe Arg Glu Trp Glu Ala Asp Pro Thr Asn Pro Ala Leu Arg Glu
        115                 120                 125
Glu Met Arg Ile Gln Phe Asn Asp Met Asn Ser Ala Leu Thr Thr Ala
    130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                165                 170                 175
Val Phe Gly Gln Arg Trp Gly Phe Asp Ala Ala Thr Ile Asn Ser Arg
            180                 185                 190
Tyr Asn Asp Leu Thr Arg Leu Ile Gly Asn Tyr Thr Asp Tyr Ala Val
        195                 200                 205
Arg Trp Tyr Asn Thr Gly Leu Glu Arg Val Trp Gly Pro Asp Ser Arg
    210                 215                 220
Asp Trp Val Arg Tyr Asn Gln Phe Arg Arg Glu Leu Thr Leu Thr Val
225                 230                 235                 240
Leu Asp Ile Val Ala Leu Phe Pro Asn Tyr Asp Ser Arg Arg Tyr Pro
                245                 250                 255
Ile Arg Thr Val Ser Gln Leu Thr Arg Glu Ile Tyr Thr Asn Pro Val
            260                 265                 270
Leu Glu Asn Phe Asp Gly Ser Phe Arg Gly Ser Ala Gln Gly Ile Glu
        275                 280                 285
Arg Ser Ile Arg Ser Pro His Leu Met Asp Ile Leu Asn Ser Ile Thr
    290                 295                 300
Ile Tyr Thr Asp Ala His Arg Gly Tyr Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Leu Tyr Arg
        355                 360                 365
Arg Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
        435                 440                 445
Arg Ala Pro Met Phe Ser Trp Ile His Arg Ser Ala Glu Phe Asn Asn
    450                 455                 460
```

-continued

```
Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
            485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
        530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
            595                 600                 605

Val Thr Phe Glu
        610
```